US012582672B2

(12) United States Patent
Corsello et al.

(10) Patent No.: US 12,582,672 B2
(45) Date of Patent: Mar. 24, 2026

(54) VANADIUM COMPOSITIONS AND METHODS FOR TREATMENT OF CANCER

(71) Applicants: THE BROAD INSTITUTE, INC., Cambridge, MA (US); DANA-FARBER CANCER INSTITUTE, INC.; INSTITUTO CARLOS SLIM DE LA SALUD, A.C., Mexico City (MX)

(72) Inventors: Steven Corsello, Boston, MA (US); Ryan Spangler, Cambridge, MA (US); Rohith Nagari, Cambridge, MA (US); Todd Golub, Cambridge, MA (US)

(73) Assignees: The Broad Institute, Inc., Cambridge, MA (US); Dana-Farber Cancer Institute, Inc., Boston, MA (US); Instituto Carlos Slim de la Salud, A.C., Mexico City (MX)

( * ) Notice: Subject to any disclaimer, the term of this patent is extended or adjusted under 35 U.S.C. 154(b) by 1350 days.

(21) Appl. No.: 17/293,375

(22) PCT Filed: Nov. 13, 2019

(86) PCT No.: PCT/US2019/061108
§ 371 (c)(1),
(2) Date: May 12, 2021

(87) PCT Pub. No.: WO2020/102295
PCT Pub. Date: May 22, 2020

(65) Prior Publication Data

US 2022/0008457 A1 Jan. 13, 2022

Related U.S. Application Data

(60) Provisional application No. 62/767,345, filed on Nov. 14, 2018.

(51) Int. Cl.
*A61K 33/24* (2019.01)
*A61K 31/555* (2006.01)
(Continued)

(52) U.S. Cl.
CPC .............. *A61K 33/24* (2013.01); *A61P 35/00* (2018.01); *C12Q 1/6886* (2013.01);
(Continued)

(58) Field of Classification Search
CPC ....... A61K 33/24; A61P 35/00; C12Q 1/6886; C12Q 2600/158
See application file for complete search history.

(56) References Cited

U.S. PATENT DOCUMENTS

2004/0110155 A1* 6/2004 Dobie .................... C07H 21/04 435/6.16

FOREIGN PATENT DOCUMENTS

WO 1997/47296 A2 12/1997
WO WO-2009025847 A2 * 2/2009 ......... G01N 33/5041
WO 2018/064762 A1 4/2018

OTHER PUBLICATIONS

Maxwell et al "Microarray Analysis of Endometrial Carcinomas and Mixed Mullerian Tumors Reveals Distinct Gene Expression Profiles Associated with Different Histologic Types of Uterine Cancer." Clinical cancer research 11.11 (2005): 4056-406 (Year: 2005).*

(Continued)

*Primary Examiner* — Savitha M Rao
*Assistant Examiner* — Elena Vladimirovna Vishnyakova
(74) *Attorney, Agent, or Firm* — GTC Law Group PC & Affiliates

(57) ABSTRACT

The present disclosure relates to compositions and methods for the diagnosis and treatment or prevention of cancers, particularly cancers that exhibit elevated expression of SLC26A2, such as certain ovarian, endometrial, brain, bone,
(Continued)

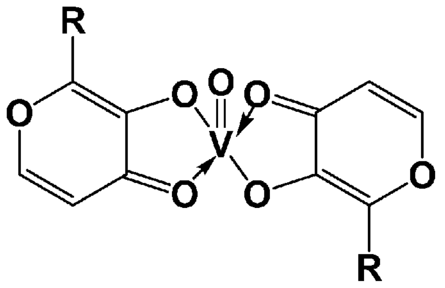

R=$CH_3$, BMOV, VO(ma)$_2$

R=$C_2H_5$, BEOV, VO(ema)$_2$

**R=*i*-$C_3H_7$, BIOV, VO(ipma)$_2$**

**R=*n*-$C_4H_9$, BnBOV, VO(nbma)$_2$** and lung cancers, as well as melanoma. A previously identified vanadium-containing compound, bis(maltolato)oxovanadium(IV) (BMOV), specifically provided for killing of SLC26A2 expressing cancer cells in a SLC26A2-dependent manner. The instant disclosure therefore provides for selecting and/or administering BMOV and related vanadium-containing compounds as a therapeutic agent to target a cancer cell and/or subject having or at risk of developing a cancer. Methods and compositions for therapies that include such compounds are also provided.

18 Claims, 11 Drawing Sheets

Specification includes a Sequence Listing.

(51) Int. Cl.
*A61P 35/00* (2006.01)
*C12Q 1/6886* (2018.01)
*G01N 33/574* (2006.01)

(52) U.S. Cl.
CPC . *G01N 33/57492* (2013.01); *C12Q 2600/106* (2013.01); *C12Q 2600/158* (2013.01); *G01N 2800/52* (2013.01)

(56) References Cited

OTHER PUBLICATIONS

Jackson, J K et al. A Polymer-Based Drug Delivery System for the Antineoplastic Agent Bis (Maltolato) Oxovanadium in Mice. Apr. 1, 1997.
Extended European Search Report in corresponding EP application No. 19884768.3 dated Jul. 21, 2022.
International Search Report dated Jan. 29, 2020 for related Application No. PCT/US2019/061108.
Dimberg LY et al. ‘A Genome-Wide Loss-of-Function Screen Identifies SLC26A2 as a Novel Mediator of TRAIL Resistance’; Jan. 20, 2017, Molecular Cancer Research; vol. 15, Issue 4, pp. 382-394; abstract; p. 384, first column fourth paragraph; p. 389, first column, first paragraph; p. 391, table 1; p. 393, first column, second paragraph.
Corsello, SM et al. ‘Non-oncology drugs are a source of previously unappreciated anti-cancer activity’; Aug. 9, 2019, Biorxiv; pp. 1-41; entire document.
Examination Report in corresponding EP application No. 19884768.3 dated Jun. 19, 2024.

* cited by examiner

R=$CH_3$, BMOV, VO(ma)$_2$

R=$C_2H_5$, BEOV, VO(ema)$_2$

**R=*i*-$C_3H_7$, BIOV, VO(ipma)$_2$**

**R=*n*-$C_4H_9$, BnBOV, VO(nbma)$_2$**

| Number of Points | Pearson | Spearman | Slope | Intercept | p-value (linregress) |
|---|---|---|---|---|---|
| 484 | -0.573 | -0.476 | -3.12E-1 | 5.28E-1 | 1.57E-43 |

| Cell_line | AUC | IC50 (uM) | % viability at 2.5 uM | SLC26A2 expression (log2 TPM) |
|---|---|---|---|---|
| OVISE_OVARY | 0.68 | 0.39 | 11.63 | 6.15 |
| UACC62_SKIN | 0.70 | 0.55 | 14.32 | 5.39 |
| A673_BONE | 0.73 | 0.55 | 23.14 | 6.41 |
| A375_SKIN | 0.73 | 0.72 | 10.41 | 7.27 |
| WM793_SKIN | 074 | 0.73 | 8.31 | 4.43 |
| HEC59_ENDOMETRIUM | 0.76 | 0.76 | 12.23 | 4.56 |
| SH4_SKIN | 0.77 | 1.00 | 9.68 | 4.43 |
| HS944T_SKIN | 0.78 | 0.99 | 10.77 | 6.05 |
| HEC151_ENDOMETRIUM | 0.78 | 1.13 | 17.86 | 5.71 |
| NCIH1650_LUNG | 0.79 | 0.66 | 30.58 | 4.18 |
| NCIH1693_LUNG | 0.79 | 1.46 | 37.76 | 5.42 |
| WM88_SKIN | 0.79 | 1.32 | 26.96 | 7.54 |
| HEC251_ENDOMETRIUM | 0.79 | 1.06 | 32.13 | 4.22 |
| COLO800_SKIN | 0.80 | 1.29 | 20.52 | 5.18 |
| SNU738_CENTRAL_NERVOUS_SYSTEM | 0.80 | 1.31 | 27.79 | 4.57 |
| RL952_ENDOMETRIUM | 0.80 | 1.37 | 19.66 | 5.59 |
| LN229_CENTRAL_NERVOUS_SYSTEM | 0.80 | 1.38 | 24.94 | 5.77 |
| 253J_URINARY_TRACT | 0.81 | 1.43 | 26.89 | 5.47 |
| MDAMB435S_SKIN | 0.81 | 1.44 | 22.28 | 7.02 |
| NCIH2172_LUNG | 0.81 | 1.31 | 18.20 | 4.73 |
| A101D_SKIN | 0.81 | 1.56 | 26.48 | 4.86 |
| IGROV1_OVARY | 0.82 | 1.75 | 37.10 | 6.34 |
| A2058_SKIN | 0.82 | 1.58 | 21.51 | 6.28 |
| RERFLCKJ_LUNG | 0.82 | 1.57 | 30.97 | 4.14 |
| TOV21G_OVARY | 0.82 | 1.60 | 10.97 | 4.50 |

FIG. 3

SEQUENCE LISTING

<160> NUMBER OF SEQ ID NOS: 2

<210> SEQ ID NO 1
<211> LENGTH: 8082
<212> TYPE: DNA
<213> ORGANISM: Homo sapiens

<400> SEQUENCE: 1
gtgacggcct cggccgcggg cgtttacact ggctctgcct ccggcatctc ttcgccggtg 60
cgtcctcgcc gcgcccgtag gtcccggcag ccgggccccg cctccttcgg agtccgagcg 120
atgggcgggg aaagggacag gcaggtatag ctctgtcggc gccgcggtgt ccacctcagt 180
caggccacgg tggaagacgc gtgccgcggc gcctggttgc ctgcagcggc ccggacccga 240
gaggaagctg aaccatctat ctccagaaat gtcttcagaa agtaaagagc aacataacgt 300
ttcacccaga gactcagctg aaggaaatga cagttatcca tctgggatcc atctggaact 360
tcaaagggaa tcaagtactg acttcaagca atttgagacc aatgatcaat gcagacctta 420
tcataggatc cttattgagc gtcaagagaa atcagataca aacttcaagg agtttgttat 480
taaaaagctg cagaagaatt gccagtgcag tccagccaaa gccaaaaata tgattttagg 540
tttccttcct gttttgcagt ggctcccaaa atacgaccta aagaaaaaca ttttagggga 600
tgtgatgtca ggcttgattg tgggcatatt attggtgccc cagtccattg cttattccct 660
gctggctggc caagaacctg tctatggtct gtacacatct ttttttgcca gcatcattta 720
ttttctcttg ggtacctccc gtcacatctc tgtgggcatt tttggagtac tgtgccttat 780
gattggtgag acagttgacc gagaactaca gaaagctggc tatgacaatg cccatagtgc 840
tccttcctta ggaatggttt caaatgggag cacattatta aatcatacat cagacaggat 900
atgtgacaaa agttgctatg caattatggt tggcagcact gtaaccttta tagctggagt 960
ttatcaggta gcgatgggct tctttcaagt gggttttgtt tctgtctacc tctcagatgc 1020

-continued cttgctgagt ggatttgtca ctggtgcctc cttcactatt cttacatctc aggccaagta 1080
tcttcttggg ctcaaccttc ctcggactaa tggtgtgggc tcactcatca ctacctggat 1140
acatgtcttc agaaacatcc ataagaccaa tctctgtgat cttatcacca gccttttgtg 1200
ccttttggtt cttttgccaa ccaaagaact caatgaacac ttcaaatcca agcttaaggc 1260
accgattcct attgaacttg ttgttgttgt agcagccaca ttagcctctc attttggaaa 1320
actacatgaa aattataatt ctagtattgc tggacatatt cccactgggt ttatgccacc 1380
caaagtacca gaatggaacc taattcctag tgtggctgta gatgcaatag ctatttccat 1440
cattggtttt gctatcactg tatcactttc tgagatgttt gccaagaaac atggttacac 1500
agtcaaagca aaccaggaaa tgtatgccat tggcttttgt aatatcatcc cttccttctt 1560
ccactgtttt actactagtg cagctcttgc aaagacattg gttaaagaat caacaggctg 1620
ccatactcag ctttctggtg tggtaacagc cctggttctt ttgttggtcc tcctagtaat 1680
agctcctttg ttctattccc ttcaaaaaag tgtccttggt gtgatcacaa ttgtaaatct 1740
acggggagcc cttcgtaaat ttagggatct tcccaaaatg tggagtatta gtagaatgga 1800
tacagttatc tggtttgtta ctatgctgtc ctctgcactg ctaagtactg aaataggcct 1860
acttgttggg gtttgttttt ctatattttg tgtcatcctc cgcactcaga agccaaagag 1920
ttcactgctt ggcttggtgg aagagtctga ggtctttgaa tctgtgtctg cttacaagaa 1980
ccttcagatt aagccaggca tcaagatttt ccgctttgta gcccctctct actacataaa 2040
caaagaatgc tttaaatctg ctttatacaa acaaactgtc aacccaatct taataaaggt 2100
ggcttggaag aaggcagcaa agagaaagat caaagaaaaa gtagtgactc ttggtggaat 2160
ccaggatgaa atgtcagtgc aactttccca tgatcccttg gagctgcata ctatagtgat 2220
tgactgcagt gcaattcaat ttttagatac agcagggatc cacacactga aagaagttcg 2280
cagagattat gaagccattg gaatccaggt tctgctggct cagtgcaatc ccactgtgag 2340
ggattcccta accaacggag aatattgcaa aaaggaagaa gaaaaccttc tcttctatag 2400
tgtgtatgaa gcgatggctt ttgcagaagt atctaaaaat cagaaaggag tatgtgttcc 2460
caatggtctg agtcttagta gtgattaatt gagaaggtag atagaagaat gtctagccaa 2520
taggttaaaa tttcaagtgt ccaacatttc ccagttccac agtgggaaat tttgcacact 2580
tgaaatttta accaagtggc tagatattat tcctcctttg aagctaatgg catttgtata 2640
tacacactgc agcagagctt gtagctggac agagtcaaaa agaagaaaat acggtttcag 2700
gctttcttgc agatatgaag tattcttgga atgcaataag tatgtattga actgtactgt 2760
aaagtagctc caaaacttaa ttactctcct gttttagggg ttatacattt ggactgtgca 2820
ttctccaaga gatgaagcgg tgaagttggg atttacattg gaagtgctgt agacttcttt 2880
atgtggctca gtggagagag ggaaagaatg ttgcacctgc tctagtacca taggtcaaga 2940
ggcttctgga tcacaaagtc ataactagac aggtttgttc ttgtagtttt ctatccccag 3000
tctttgctcc ccagatggca gtagttttta gtaggaaagt gccattcctg tccttaaggc 3060
acagtctcat cagaagtcta atacctgggc aggtttataa catcctgaga gccagcctga 3120
cattagacag aataccettt gtaatacatt ggaaattttt actcatgcct ttttgtttag 3180
gataaatagg taagcacaaa gagctcttca aaatcagaaa aaacaatagg agtccttcct 3240
tgtcttttct gtgatctctg tccttgtttc tgagactttc tctaccatta agctctattt 3300
tagctttcag ttattctagt ttgtttccca tggaatctgt cctaaactgg tgtttttgtc 3360

-continued

```
agtgacagtc ttgccagtca gcaatttcta acagcatttt aaatgagttt gatgtacagt   3420
aaatattgat gacaatgaca gcttttaact cttcaagtca cctaaagcta ttatgcagga   3480
ggatttagaa gtcacattca taaaacccaa gtgctatggg tgtattattc atgatagctg   3540
gcccacaggt catgaattga ggaggaattt gctttcaaaa agcaagaatg tccaacactg   3600
aaagtttata gttttatatt tggaccttga aaggtaagaa aaaaccaggt tctccaaagt   3660
taggaatagg gaactaattt atgaaacagc catcttaaaa aaaaaaaaag taaactgcaa   3720
aagtacaaaa tcatttttca atctgttccc agtttctaaa caattttaaa tatttatgag   3780
aagcaaaccc tatgtgtagg gcatctgttg gagtgggatg cttttagaca tatattaagt   3840
atgtacatgt ttaatatgta tatttaaaat gcatatatat tttattatat ctatattatc   3900
ctatatagat atatgtaact tagctttatt gttagctcca taagctgcca gtgttgcttt   3960
tctgttggta gagctctccc atttggtgac atggaaaata cctttccatt atcacaacaa   4020
agcagttgct cagtagaaag tctagatttc tgtcttatag gtgatttctg tcttataggt   4080
gattataatc aagtgtaggc ttcctgaatt ttgacatcct tttagaactt gggtctggaa   4140
ttccagaaat gttaattgct gcttgtattt gttcttgttt gtttttagc cagtatttgc    4200
cctttctatc cagccttatg aataatagca gtaaaatcac agtatcttgg tcagtcttta   4260
ttttttcct tttttctttt ttaagagaca gtcatccagg ccagagtgca gtttgatgat    4320
agcttactga agcttcccac tcctgggctc aagttatcct tccattttgg cctcctgagt   4380
agctagacca taggtatgca tcaccacacc ctgctaattt tttaaatttt tttctagaga   4440
gagggtctca ctgtgttgcc caggctggtc tcaaactcca ggctcaagca atccttcagc   4500
ctcagcctcc cagagtgttg ggattacagg cgtgagccac tgcacttggc caagttattt   4560
atttttaatc tctcttgccc ttctcccaag gcaggcttaa gttgagacta ttataggtgt   4620
ctaataacct gtgacagagt aatgagtaca tgcttaagat gttataatta gccaacacca   4680
acacagcaaa aaatataatt ccagccaaag attctggaaa atccctcaga aggagggata   4740
acaggatttg acctttacca gcgatttctg tccatatgtg gatgtaaaca gttctggaac   4800
gttatgcatg cagttagcga atccttgaat tatgttctgg tttgtacttg tcccatccat   4860
ccaaacaaga gattctgctt ttggtagcca tctgtagaaa catttaagat gtcactagaa   4920
tttacatttc atcctctcta cttgggttga ggttgcctat acttgcatat tgttaaaatg   4980
ttttggttgc tgatattcag aggaatgaaa cctggaacca aagcctaatt tgccgataaa   5040
aaaactgttt tcggccaggt gcagtggctc atgcctgtaa tcccagcacg ttgggaggcc   5100
gaggcgggtg gatcacctga agtcaggagt tcgagaccat cctggctaac actgtgaaac   5160
cccgtctcta ctaaaaatac aaaaaattag cggggcatgg tggcacgcgc ctgtagtccc   5220
agctactcag gaggctgagg caggagaatt acttgaaccc gggaggcgga ggttgcagta   5280
agcagagatt gtgccactgg actccagcct gggtgacaga gcgagactcc gtctcaaaca   5340
aacaaacaaa aaactgtttt catttgctct cttgaccaaa ggataggact ttagttcttt   5400
aagcattatt ttaaacacta tattgataca aaaatatctt gcttactcta aactttagag   5460
tctaaatgaa gctttttctc agtacaagat tctgagtatc ataaaatggt tatttaattg   5520
aaacgtagtg tggtatactc ttgatggtta gaactcttac agccttattt atttttaagt   5580
ttgttacagc caaagggttg gagtgtgcca gtgcacaggt agactaagga aaacattata   5640
gaggagtgaa gagaacagac cattgaaaag actattatct gaccagcgga ggcagaaaag   5700
agaggaaccc agttgaatag gatccaatcc ctggttagcc tctacacaat aatagggaga   5760
```

-continued

```
caaggattag gagccatacc tcccagagca aggtatcttt ctagagcaaa tttctctttc   5820
tagaagggga gggtcacagg gtcacagatt caccaaagct gaaagggctg aggagctcat   5880
ggtagcctgg gctgacctac tctggagcac ggtgtcttcc ttctaaactg agtgactgta   5940
gtactatctg tgcctctgat ggtaataaaa ctgacaagat gtctaatttt tttttaagta   6000
ggaccaaagg aaaacaagat ttagatagtc tgactttgct tttgaacaac agacattgca   6060
agtcaaaatt gttgtcaaat ttacatatgg taaatgatga actttaaaaa tgtgtccagg   6120
tgttagatga gttcattaga ctcttttaat gctaatggct agtacgttta aacaaaacag   6180
cagttctctg ctgcaatatt cccattgacc acttaaatga ccataagtgg tcatttaaga   6240
acatgttagg gttagccctg atctgaatat aaaagtgaga aaagggctac agtgcatttc   6300
ttggtaactt aaactgagtc ttgaagttat aatgatccat tcgagttctg tgatccttat   6360
tgttcttaat tgtgtttctc tacgtattgt tacagatgag ccatacgttt ctttgtatca   6420
atgtagacat gacttcagat acctctgagg acctacccag cagtctagga ccctgggcca   6480
agtgctggga ctatggtact aaatccagta gatgggctgt gtagcaactc tcccagggaa   6540
cacactaggg tacttaggga ggtgctttgt ggagcatgtt gaagctttga gatctgagca   6600
ggaggcagtg atgtccctgg tctattcagg gaaagatttc agtgtgaaat ggtaaacatc   6660
caattgacag gatttagatt ttgcttagtt tttctgcttt ttaatgtttc tatcccccat   6720
ctcagtgttt tctttatcca tcccagtgat gccttatttg aaactgggct taaactgcaa   6780
aaagaatgaa gttggattta ggaagctgtt agatcattga gtggtgttga gagtgaagtt   6840
tcactagcag ggaagtttcc ttgagcctaa aataaaaaga aaaaattaaa aagaatcagt   6900
ttttttaatt aaaaaaatag aaagctgtta ggctcctaat tcgtggggtt tttttttgta   6960
aaaacagttt agataatcct gaatgcaatc attaacttgg ttgctaatta caagaatgaa   7020
aattataatg gaaaaggaca aaataatata ccagctggtt tgttattata gtccgtgtat   7080
taaaatacta ttgaaatacg ttaaaggtaa atttttaagg tttaaaaaaa atttagtaac   7140
ttacagggat ggagaattta gatgtcagag gtggggagat ttatttttat aaggtaattt   7200
ttatcctgat aaggacttaa aaaaaagttt tgcaactgaa attttaaagt aaacatgtta   7260
agtacagtta aaaagtaagc attgtagtaa atagtggatt ctctggtgtg tatttttttat   7320
ctcagtgttg aaaattggaa aagaatggac tgaagtctaa aaactggaat aatgaaggac   7380
actaaatgcc tttattgtag atactatgtt tgtaagtcta tagctaagca acttaagcca   7440
aaaaggtctt tcaactgaag ctttaatcaa cttattttgg agatgttctc ttcccttatc   7500
tcatgcgtca tccctaaaat aataagatac atgggatcaa atagcccttg ccttttcaac   7560
acaaatcagt tggaaaatta tggtttgagt cctgttgctg ccatggcttc tgtttctcag   7620
aaatgagtgt gtatgaacat accaatctat gtaataggct acctttttttt gtcttctttg   7680
gaactttgta cacaaaccaa gacaatatca gggtgacagg tgaatgaact taaattctca   7740
gtcttgtcta ttcaccaaaa aagtatactg cctgtttttt ctttaattat tcaaggttga   7800
tgacttttag gaacatgttt tatactgtat tttttaatta aagcaagtgc cttgatgtaa   7860
ttccatgtaa atcattgctt aaccctctta tgggatgagg atgagttatt aatgtattgc   7920
agcctactgg aaaggagggg gagttggtta atagcagata cttttcttct agaagcttat   7980
gttttatgct gtttattatg taagatcctg tatgtgtgtt gagatttaga ggtttcattt   8040
gttttgtctg ctaataaatt gttactctaa taataaaaaa aa                       8082
```

<210> SEQ ID NO 2
<211> LENGTH: 739
<212> TYPE: PRT
<213> ORGANISM: Homo sapiens

<400> SEQUENCE: 2

Met Ser Ser Glu Ser Lys Glu Gln His Asn Val Ser Pro Arg Asp Ser
1               5                   10                  15

Ala Glu Gly Asn Asp Ser Tyr Pro Ser Gly Ile His Leu Glu Leu Gln
            20                  25                  30

Arg Glu Ser Ser Thr Asp Phe Lys Gln Phe Glu Thr Asn Asp Gln Cys
        35                  40                  45

Arg Pro Tyr His Arg Ile Leu Ile Glu Arg Gln Glu Lys Ser Asp Thr
    50                  55                  60

Asn Phe Lys Glu Phe Val Ile Lys Lys Leu Gln Lys Asn Cys Gln Cys
65                  70                  75                  80

Ser Pro Ala Lys Ala Lys Asn Met Ile Leu Gly Phe Leu Pro Val Leu
                85                  90                  95

Gln Trp Leu Pro Lys Tyr Asp Leu Lys Lys Asn Ile Leu Gly Asp Val
            100                 105                 110

Met Ser Gly Leu Ile Val Gly Ile Leu Leu Val Pro Gln Ser Ile Ala
        115                 120                 125

Tyr Ser Leu Leu Ala Gly Gln Glu Pro Val Tyr Gly Leu Tyr Thr Ser
    130                 135                 140

Phe Phe Ala Ser Ile Ile Tyr Phe Leu Leu Gly Thr Ser Arg His Ile
145                 150                 155                 160

Ser Val Gly Ile Phe Gly Val Leu Cys Leu Met Ile Gly Glu Thr Val
                165                 170                 175

Asp Arg Glu Leu Gln Lys Ala Gly Tyr Asp Asn Ala His Ser Ala Pro
            180                 185                 190

Ser Leu Gly Met Val Ser Asn Gly Ser Thr Leu Leu Asn His Thr Ser
        195                 200                 205

Asp Arg Ile Cys Asp Lys Ser Cys Tyr Ala Ile Met Val Gly Ser Thr
    210                 215                 220

Val Thr Phe Ile Ala Gly Val Tyr Gln Val Ala Met Gly Phe Phe Gln
225                 230                 235                 240

Val Gly Phe Val Ser Val Tyr Leu Ser Asp Ala Leu Leu Ser Gly Phe
                245                 250                 255

Val Thr Gly Ala Ser Phe Thr Ile Leu Thr Ser Gln Ala Lys Tyr Leu
            260                 265                 270

Leu Gly Leu Asn Leu Pro Arg Thr Asn Gly Val Gly Ser Leu Ile Thr
        275                 280                 285

Thr Trp Ile His Val Phe Arg Asn Ile His Lys Thr Asn Leu Cys Asp
    290                 295                 300

Leu Ile Thr Ser Leu Leu Cys Leu Leu Val Leu Leu Pro Thr Lys Glu
305                 310                 315                 320

Leu Asn Glu His Phe Lys Ser Lys Leu Lys Ala Pro Ile Pro Ile Glu
                325                 330                 335

Leu Val Val Val Val Ala Ala Thr Leu Ala Ser His Phe Gly Lys Leu
            340                 345                 350

His Glu Asn Tyr Asn Ser Ser Ile Ala Gly His Ile Pro Thr Gly Phe
        355                 360                 365

Met Pro Pro Lys Val Pro Glu Trp Asn Leu Ile Pro Ser Val Ala Val
    370                 375                 380

-continued

```
Asp Ala Ile Ala Ile Ser Ile Ile Gly Phe Ala Ile Thr Val Ser Leu
385                 390                 395                 400

Ser Glu Met Phe Ala Lys Lys His Gly Tyr Thr Val Lys Ala Asn Gln
                405                 410                 415

Glu Met Tyr Ala Ile Gly Phe Cys Asn Ile Ile Pro Ser Phe Phe His
            420                 425                 430

Cys Phe Thr Thr Ser Ala Ala Leu Ala Lys Thr Leu Val Lys Glu Ser
        435                 440                 445

Thr Gly Cys His Thr Gln Leu Ser Gly Val Val Thr Ala Leu Val Leu
    450                 455                 460

Leu Leu Val Leu Leu Val Ile Ala Pro Leu Phe Tyr Ser Leu Gln Lys
465                 470                 475                 480

Ser Val Leu Gly Val Ile Thr Ile Val Asn Leu Arg Gly Ala Leu Arg
                485                 490                 495

Lys Phe Arg Asp Leu Pro Lys Met Trp Ser Ile Ser Arg Met Asp Thr
            500                 505                 510

Val Ile Trp Phe Val Thr Met Leu Ser Ser Ala Leu Leu Ser Thr Glu
        515                 520                 525

Ile Gly Leu Leu Val Gly Val Cys Phe Ser Ile Phe Cys Val Ile Leu
    530                 535                 540

Arg Thr Gln Lys Pro Lys Ser Ser Leu Leu Gly Leu Val Glu Glu Ser
545                 550                 555                 560

Glu Val Phe Glu Ser Val Ser Ala Tyr Lys Asn Leu Gln Ile Lys Pro
                565                 570                 575

Gly Ile Lys Ile Phe Arg Phe Val Ala Pro Leu Tyr Tyr Ile Asn Lys
            580                 585                 590

Glu Cys Phe Lys Ser Ala Leu Tyr Lys Gln Thr Val Asn Pro Ile Leu
        595                 600                 605

Ile Lys Val Ala Trp Lys Lys Ala Ala Lys Arg Lys Ile Lys Glu Lys
    610                 615                 620

Val Val Thr Leu Gly Gly Ile Gln Asp Glu Met Ser Val Gln Leu Ser
625                 630                 635                 640

His Asp Pro Leu Glu Leu His Thr Ile Val Ile Asp Cys Ser Ala Ile
                645                 650                 655

Gln Phe Leu Asp Thr Ala Gly Ile His Thr Leu Lys Glu Val Arg Arg
            660                 665                 670

Asp Tyr Glu Ala Ile Gly Ile Gln Val Leu Leu Ala Gln Cys Asn Pro
        675                 680                 685

Thr Val Arg Asp Ser Leu Thr Asn Gly Glu Tyr Cys Lys Lys Glu Glu
    690                 695                 700

Glu Asn Leu Leu Phe Tyr Ser Val Tyr Glu Ala Met Ala Phe Ala Glu
705                 710                 715                 720

Val Ser Lys Asn Gln Lys Gly Val Cys Val Pro Asn Gly Leu Ser Leu
                725                 730                 735

Ser Ser Asp
```

VANADIUM COMPOSITIONS AND METHODS FOR TREATMENT OF CANCER

CROSS REFERENCE TO RELATED APPLICATIONS

This application is a national stage application, filed under 35 U.S.C. § 371, of international application No. PCT/US2019/061108, filed Nov. 13, 2019, which claims the benefit of U.S. Provisional Application No. 62/767,345, filed Nov. 14, 2018, entitled "Vanadium Compositions and Methods for Treatment of Cancer," the entire contents of which are incorporated herein by reference.

FIELD OF THE DISCLOSURE

The disclosure relates generally to compositions, methods, and kits for the identification and treatment of cancer. More particularly, the disclosure relates to vanadium compositions and methods for the treatment of Solute Carrier Family 26 Member 2 (SLC26A2)-dependent and/or overexpressing cancers.

BACKGROUND OF THE DISCLOSURE

By the year 2020, it is estimated that nearly 18.2 million U.S. citizens will be either cancer patients or cancer survivors. A significant proportion of those affected by cancer will involve solid tumors-abnormal masses of tissue that usually do not contain cysts or liquid areas such as, for example, sarcomas, carcinomas, lymphomas, and the like. Unfortunately, advanced solid tumors remain largely incurable, with the majority of treatment options focused on palliation. Identifying therapeutic compounds capable of killing neoplastic cells (e.g., solid tumors) in an optimally selective manner poses an ongoing challenge for the oncology field. A need exists for agents that are capable of precision killing of neoplastic cells that are characterized by specific molecular traits.

BRIEF SUMMARY OF THE DISCLOSURE

The present disclosure is based, at least in part, on the discovery that certain types of cancer (e.g., ovarian cancer, endometrial cancer, brain cancer, bone cancer, lung cancer, melanoma, and the like), particularly those characterized by high expression and/or overexpression of SLC26A2 are particularly susceptible to treatment with vanadium-containing drugs. In particular, bis(maltolato)oxovanadium(IV) (BMOV) was identified via genomic screening methods as a vanadium-containing agent among drugs present in a drug repurposing library that exhibited progressively enhanced killing of neoplasia cell lines as SLC26A2 expression levels rose across such screened neoplasia cell lines. Cancers particularly including ovarian cancer, endometrial cancer, brain cancer, bone cancer, lung cancer, and melanoma, among others, have therefore herein been identified as susceptible to treatment with vanadium-containing drugs such as, for example, BMOV, bis(ethylmaltolato)oxovanadium(IV) (BEOV), bis(isopropylmaltolato)oxovanadium (IV), (BIOV), and bis(n-butylmaltolato)oxovanadium(IV) (BnBOV), and the like. A. Such cancers particularly include ovarian cancer, bone cancer, and melanoma. The instant disclosure therefore provides compositions and methods for the diagnosis and treatment of cancer that employ vanadium-containing drugs having the general structure of Formula (I)

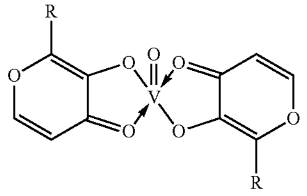

(I) (e.g., as a monotherapy, optionally in certain classes of cancer, such as SLC26A2-positive cancer) or in combination with other chemotherapeutic drugs.

In one aspect, the disclosure provides a method for selecting a treatment for a subject having or at risk of developing a Solute Carrier Family 26 Member 2 (SLC26A2) positive cancer, the method including the steps of: (a) identifying a subject as having or at risk of developing the Solute Carrier Family 26 Member 2 (SLC26A2) positive cancer; and (b) selecting a compound of Formula (I)

(I)

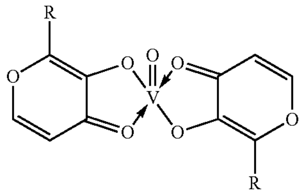

as a treatment for the subject identified as having or at risk of developing the Solute Carrier Family 26 Member 2 (SLC26A2) positive cancer.

In one aspect, the disclosure provides a method for selecting a treatment for a subject having or at risk of developing a cancer, the method including the steps of: (a) obtaining a sample from a subject having or at risk of developing a cancer; (b) identifying the presence or absence in the sample of high SLC26A2 mRNA expression levels; and (c) selecting moiety compound of Formula (I)

(I)

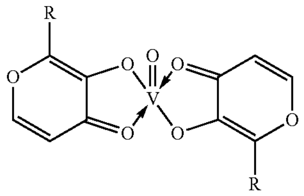

as a treatment for the subject if high SLC26A2 mRNA expression levels are observed in the sample, thereby selecting a treatment for the subject having or at risk of developing a cancer.

In embodiments, R may be selected from the group consisting of $CH_3$, $C_2H_5$, i-$C_3H_7$, and n-$C_4H_9$.

In embodiments, the cancer may be selected from the group consisting of an ovarian cancer, an endometrial cancer, a brain cancer, a bone cancer, a lung cancer, and a melanoma.

In embodiments, step (b) may include identifying the presence or absence in the sample of elevated SLC26A2 mRNA expression, as compared to an appropriate control.

In embodiments, a compound selected from

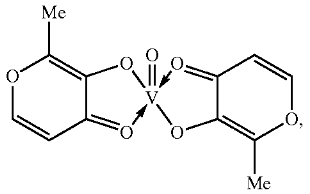

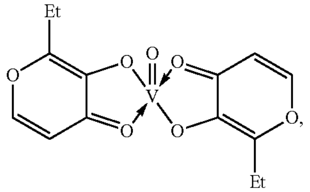

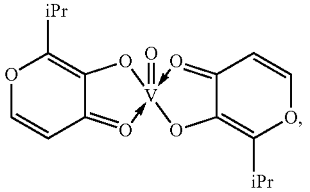

or

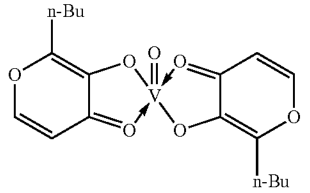

-continued

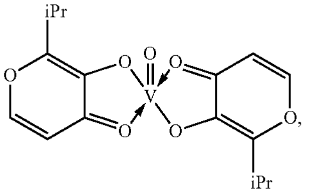

or

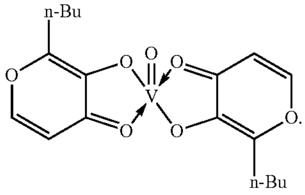

is selected as a treatment for the subject.

In embodiments, the method further includes the step of: (c) administering the selected compound of Formula (I)

(I)

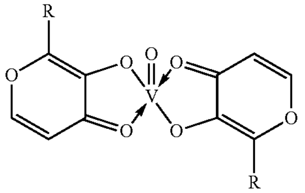

to the subject.

In embodiments, the compound of formula (I) is

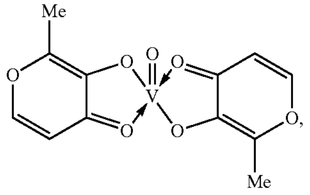

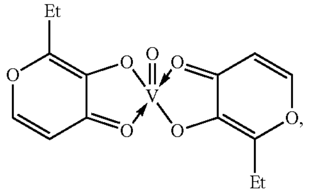

In embodiments, the compound of formula (I) is

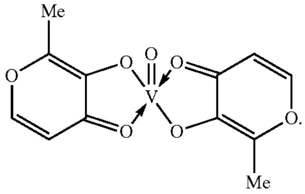

In embodiments, the subject is human.

In one aspect, the disclosure provides a method for treating or preventing a Solute Carrier Family 26 Member 2 (SLC26A2) positive cancer in a subject, the method including the steps of: (a) identifying a subject as having or at risk of developing the Solute Carrier Family 26 Member 2 (SLC26A2) positive cancer; and (b) administering a compound of Formula (I)

(I)

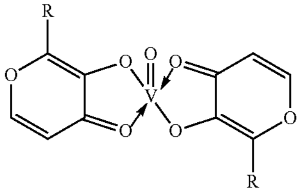

to the subject identified as having or at risk of developing the Solute Carrier Family 26 Member 2 (SLC26A2) positive cancer, thereby treating or preventing the SLC26A2 positive cancer in the subject.

In one aspect, the disclosure provides a method for treating or preventing a cancer in a subject, the method including the steps of: (a) obtaining a sample from a subject having or at risk of developing a cancer; (b) identifying the presence or absence in the sample high SLC26A2 mRNA expression levels; and (c) administering a compound of Formula (I)

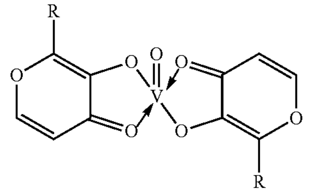

(I)

to the subject if high SLC26A2 mRNA expression levels are observed in the sample, thereby treating or preventing a cancer in the subject.

In embodiments, the cancer is selected from the group consisting of an ovarian cancer, an endometrial cancer, a brain cancer, a bone cancer, a lung cancer, and a melanoma.

In embodiments, R may be selected from the group consisting of $CH_3$, $C_2H_5$, $i\text{-}C_3H_7$, and $n\text{-}C_4H_9$.

In embodiments, the compound of formula (I) is

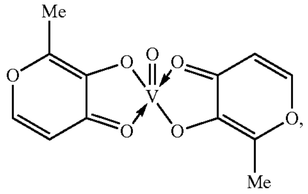

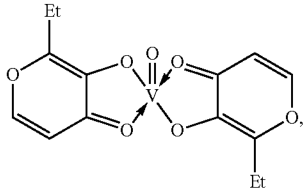

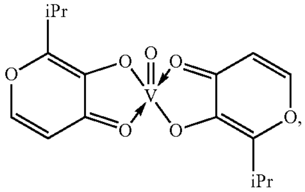

or

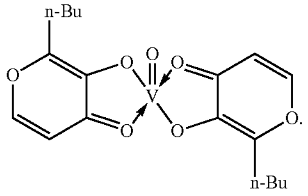

In one aspect, the disclosure provides a kit for identifying high expression of SLC26A2 mRNA or protein in a sample consisting essentially of an oligonucleotide for detection of SLC26A2 mRNA or an anti-SLC26A2 antibody (optionally labeled or wherein the kit comprises a labeled secondary antibody that binds the anti-SLC26A2 antibody), and instructions for its use.

In embodiments, the sample is a cancer sample, optionally wherein the cancer sample is selected from the group consisting of an ovarian cancer, an endometrial cancer, a brain cancer, a bone cancer, a lung cancer, and a melanoma, optionally wherein the cancer sample is a SLC26A2 positive cancer sample.

In embodiments, the sample is a tissue sample of a subject having a cancer selected from the group consisting of an ovarian cancer, an endometrial cancer, a brain cancer, a bone cancer, a lung cancer, and a melanoma.

In one aspect, the disclosure provides a pharmaceutical composition for treating a subject having a SLC26A2 positive cancer selected from the group consisting of an ovarian cancer, an endometrial cancer, a brain cancer, a bone cancer, a lung cancer, and a melanoma, the pharmaceutical composition comprising a therapeutically effective amount of

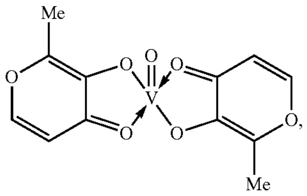

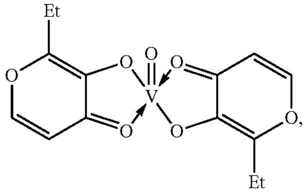

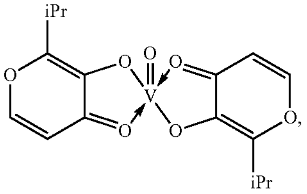

or

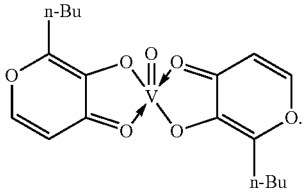

and a pharmaceutically acceptable carrier.

In embodiments, the cancer is a SLC26A2 positive cancer.

In embodiments, the subject is human.

In embodiments, any of the above identifying steps may include use of any of the above-described kits.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intra-arterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, melanoma and ovarian cancer (e.g., cystadenocarcinoma, ovarian embryonal carcinoma, ovarian adenocarcinoma), with ovarian cancer specifically including clear cell ovarian cancer. Additional exemplary cancers include, but are not limited to, colorectal cancer (e.g., colon cancer, rectal cancer, colorectal adenocarcinoma), endometrial cancer (e.g., uterine cancer, uterine sarcoma), esophageal cancer (e.g., adenocarcinoma of the esophagus, Barrett's adenocarcinoma), and gastric cancer (e.g., stomach adenocarcinoma (STAD)), including, e.g., colon adenocarcinoma (COAD), esophageal carcinoma (ESCA), rectal adenocarcinoma (READ) and uterine corpus endometrial carcinoma (UCEC). Other exemplary forms of cancer include, but are not limited to, diffuse large B-cell lymphoma (DLBCL), as well as the broader class of lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above, hematopoietic cancers (e.g., myeloid malignancies (e.g., acute myeloid leukemia (AML) (e.g., B-cell AML, T-cell AML), myelodysplastic syndrome, myeloproliferative neoplasm, chronic myelomonocytic leukemia (CMML) and chronic myelogenous leukemia (CML) (e.g., B-cell CML, T-cell CML)) and lymphocytic leukemia such as acute lymphocytic leukemia (ALL) (e.g., B-cell ALL, T-cell ALL) and chronic lymphocytic leukemia (CLL) (e.g., B-cell CLL, T-cell CLL)); brain cancer (e.g., meningioma, glioblastomas, glioma (e.g., astrocytoma, oligodendroglioma), medulloblastoma); lung cancer (e.g., bronchogenic carcinoma, small cell lung cancer (SCLC), non-small cell lung cancer (NSCLC), adenocarcinoma of the lung); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, luminal A breast cancer, luminal B breast cancer, estrogen receptor (ER)-positive forms of breast cancer, etc.); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); Ewing's sarcoma; ocular cancer (e.g., intraocular melanoma, retinoblastoma); familiar hypereosinophilia; gall bladder cancer; gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In embodiments, the cancer is an ovarian cancer, an endometrial cancer, a brain cancer, a bone cancer, a lung cancer, and/or a melanoma.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, er al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

By "SLC26A2 nucleic acid molecule" is meant a polynucleotide encoding a SLC26A2 polypeptide. An exemplary SLC26A2 nucleic acid molecule is provided at NCBI Accession No. NM_000112, also known as

```
>SLC26A2_mRNA, cDNA
                                                    (SEQ ID NO: 1)
gtgacggcctcggccgcgggcgtttacactggctctgcctccggcatctcttcgccggtgcgtcct

cgccgcgcccgtaggtcccggcagccgggccccgcctccttcggagtccgagcgatgggcggggaa

agggacaggcaggtatagctctgtcggcgccgcggtgtccacctcagtcaggccacggtggaagac

gcgtgccgcggcgcctggttgcctgcagcggcccggacccgagaggaagctgaaccatctatctcc

agaaatgtcttcagaaagtaaagagcaacataacgtttcacccagagactcagctgaaggaaatga

cagttatccatctgggatccatctggaacttcaaagggaatcaagtactgacttcaagcaatttga

gaccaatgatcaatgcagaccttatcataggatccttattgagcgtcaagagaaatcagatacaaa

cttcaaggagtttgttattaaaaagctgcagaagaattgccagtgcagtccagccaaagccaaaaa

tatgattttaggtttccttcctgttttgcagtggctcccaaaatacgacctaaagaaaaacatttt

aggggatgtgatgtcaggcttgattgtgggcatattattggtgccccagtccattgcttattccct

gctggctggccaagaacctgtctatggtctgtacacatctttttttgccagcatcatttattttct

cttgggtacctcccgtcacatctctgtgggcatttttggagtactgtgccttatgattggtgagac

agttgaccgagaactacagaaagctggctatgacaatgcccatagtgctccttccttaggaatggt

ttcaaatgggagcacattattaaatcatacatcagacaggatatgtgacaaaagttgctatgcaat

tatggttggcagcactgtaacctttatagctggagtttatcaggtagcgatgggcttctttcaagt

gggttttgtttctgtctacctctcagatgccttgctgagtggatttgtcactggtgcctccttcac

tattcttacatctcaggccaagtatcttcttgggctcaaccttcctcggactaatggtgtgggctc

actcatcactacctggatacatgtcttcagaaacatccataagaccaatctctgtgatcttatcac

cagccttttgtgccttttggttcttttgccaaccaaagaactcaatgaacacttcaaatccaagct

taaggcaccgattcctattgaacttgttgttgttgtagcagccacattagcctctcattttggaaa

actacatgaaaattataattctagtattgctggacatattcccactgggtttatgccacccaaagt

accagaatggaacctaattcctagtgtggctgtagatgcaatagctatttccatcattggttttgc

tatcactgtatcactttctgagatgtttgccaagaaacatggttacacagtcaaagcaaaccagga

aatgtatgccattggcttttgtaatatcatcccttccttcttccactgttttactactagtgcagc

tcttgcaaagacattggttaaagaatcaacaggctgccatactcagctttctggtgtggtaacagc

cctggttcttttgttggtcctcctagtaatagctcctttgttctattcccttcaaaaaagtgtcct

tggtgtgatcacaattgtaaatctacggggagcccttcgtaaatttagggatcttcccaaaatgtg
```

-continued gagtattagtagaatggatacagttatctggtttgttactatgctgtcctctgcactgctaagtac tgaaataggcctacttgttggggtttgtttttctatattttgtgtcatcctccgcactcagaagcc aaagagttcactgcttggcttggtggaagagtctgaggtctttgaatctgtgtctgcttacaagaa ccttcagattaagccaggcatcaagattttccgctttgtagcccctctctactacataaacaaaga atgctttaaatctgctttatacaaacaaactgtcaacccaatcttaataaaggtggcttggaagaa ggcagcaaagagaaagatcaaagaaaaagtagtgactcttggtggaatccaggatgaaatgtcagt gcaactttcccatgatcccttggagctgcatactatagtgattgactgcagtgcaattcaatttt agatacagcagggatccacacactgaaagaagttcgcagagattatgaagccattggaatccaggt tctgctggctcagtgcaatcccactgtgagggattccctaaccaacggagaatattgcaaaaagga agaagaaaaccttctcttctatagtgtgtatgaagcgatggcttttgcagaagtatctaaaaatca gaaaggagtatgtgttcccaatggtctgagtcttagtagtgattaattgagaaggtagatagaaga atgtctagccaataggttaaaatttcaagtgtccaacatttcccagttccacagtgggaaattttg cacacttgaaattttaaccaagtggctagatattattcctcctttgaagctaatggcatttgtata tacacactgcagcagagcttgtagctggacagagtcaaaaagaagaaaatacggtttcaggctttc ttgcagatatgaagtattcttggaatgcaataagtatgtattgaactgtactgtaaagtagctcca aaacttaattactctcctgttttaggggttatacatttggactgtgcattctccaagagatgaagc ggtgaagttgggatttacattggaagtgctgtagacttctttatgtggctcagtggagagagggaa agaatgttgcacctgctctagtaccataggtcaagaggcttctggatcacaaagtcataactagac aggtttgttcttgtagttttctatccccagtctttgctccccagatggcagtagtttttagtagga aagtgccattcctgtccttaaggcacagtctcatcagaagtctaatacctgggcaggtttataaca tcctgagagccagcctgacattagacagaatacccttttgtaatacattggaaatttttactcatgc ctttttgtttaggataaataggtaagcacaaagagctcttcaaaatcagaaaaaacaataggagtc cttccttgtcttttctgtgatctctgtccttgtttctgagactttctctaccattaagctctattt tagctttcagttattctagtttgtttcccatggaatctgtcctaaactggtgtttttgtcagtgac agtcttgccagtcagcaatttctaacagcattttaaatgagtttgatgtacagtaaatattgatga caatgacagcttttaactcttcaagtcacctaaagctattatgcaggaggatttagaagtcacatt cataaaacccaagtgctatgggtgtattattcatgatagctggcccacaggtcatgaattgaggag gaatttgctttcaaaaagcaagaatgtccaacactgaaagtttatagttttatatttggaccttga aaggtaagaaaaaaccaggttctccaaagttaggaatagggaactaatttatgaaacagccatctt aaaaaaaaaaaaagtaaactgcaaaagtacaaaatcatttttcaatctgttcccagtttctaaaca attttaaatatttatgagaagcaaaccctatgtgtagggcatctgttggagtgggatgcttttaga catatattaagtatgtacatgtttaatatgtatatttaaaatgcatatatattttattatatctat attatcctatatagatatatgtaacttagctttattgttagctccataagctgccagtgttgcttt tctgttggtagagctctcccatttggtgacatggaaaatacctttccattatcacaacaaagcagt tgctcagtagaaagtctagatttctgtcttataggtgatttctgtcttataggtgattataatcaa gtgtaggcttcctgaattttgacatccttttagaacttgggtctggaattccagaaatgttaattg ctgcttgtatttgttcttgtttgtttttagccagtatttgccctttctatccagccttatgaata atagcagtaaaatcacagtatcttggtcagtctttatttttttcctttttttctttttaagagaca gtcatccaggccagagtgcagtttgatgatagcttactgaagcttcccactcctgggctcaagtta tccttccattttggcctcctgagtagctagaccataggtatgcatcaccacaccctgctaatttt -continued taaatttttttctagagagagggtctcactgtgttgcccaggctggtctcaaactccaggctcaag
caatccttcagcctcagcctcccagagtgttgggattacaggcgtgagccactgcacttggccaag
ttatttatttttaatctctcttgcccttctcccaaggcaggcttaagttgagactattataggtgt
ctaataacctgtgacagagtaatgagtacatgcttaagatgttataattagccaacaccaacacag
caaaaaatataattccagccaaagattctggaaaatccctcagaaggagggataacaggatttgac
ctttaccagcgatttctgtccatatgtggatgtaaacagttctggaacgttatgcatgcagttagc
gaatccttgaattatgttctggtttgtacttgtcccatccatccaaacaagagattctgcttttgg
tagccatctgtagaaacatttaagatgtcactagaatttacatttcatcctctctacttgggttga
ggttgcctatacttgcatattgttaaaatgttttggttgctgatattcagaggaatgaaacctgga
accaaagcctaatttgccgataaaaaaactgttttcggccaggtgcagtggctcatgcctgtaatc
ccagcacgttgggaggccgaggcgggtggatcacctgaagtcaggagttcgagaccatcctggcta
acactgtgaaaccccgtctctactaaaaatacaaaaaattagcggggcatggtggcacgcgcctgt
agtcccagctactcaggaggctgaggcaggagaattacttgaacccgggaggcggaggttgcagta
agcagagattgtgccactggactccagcctgggtgacagagcgagactccgtctcaaacaaacaaa
caaaaaactgttttcatttgctctcttgaccaaaggataggactttagttctttaagcattatttt
aaacactatattgatacaaaaatatcttgcttactctaaactttagagtctaaatgaagctttttc
tcagtacaagattctgagtatcataaaatggttatttaattgaaacgtagtgtggtatactcttga
tggttagaactcttacagccttatttatttttaagtttgttacagccaaagggttggagtgtgcca
gtgcacaggtagactaaggaaaacattatagaggagtgaagagaacagaccattgaaaagactatt
atctgaccagcggaggcagaaaagagaggaacccagttgaataggatccaatccctggttagcctc
tacacaataatagggagacaaggattaggagccatacctcccagagcaaggtatctttctagagca
aatttctctttctagaaggggagggtcacagggtcacagattcaccaaagctgaaagggctgagga
gctcatggtagcctgggctgacctactctggagcacggtgtcttccttctaaactgagtgactgta
gtactatctgtgcctctgatggtaataaaactgacaagatgtctaatttttttttaagtaggacca
aaggaaaacaagatttagatagtctgactttgcttttgaacaacagacattgcaagtcaaaattgt
tgtcaaatttacatatggtaaatgatgaactttaaaaatgtgtccaggtgttagatgagttcatta
gactcttttaatgctaatggctagtacgtttaaacaaaacagcagttctctgctgcaatattccca
ttgaccacttaaatgaccataagtggtcatttaagaacatgttagggttagccctgatctgaatat
aaaagtgagaaaagggctacagtgcatttcttggtaacttaaactgagtcttgaagttataatgat
ccattcgagttctgtgatccttattgttcttaattgtgtttctctacgtattgttacagatgagcc
atacgtttctttgtatcaatgtagacatgacttcagatacctctgaggacctacccagcagtctag
gaccctgggccaagtgctgggactatggtactaaatccagtagatgggctgtgtagcaactctccc
agggaacacactagggtacttagggaggtgctttgtggagcatgttgaagctttgagatctgagca
ggaggcagtgatgtccctggtctattcagggaaagatttcagtgtgaaatggtaaacatccaattg
acaggatttagattttgcttagtttttctgctttttaatgtttctatcccccatctcagtgttttc
tttatccatcccagtgatgccttatttgaaactgggcttaaactgcaaaaagaatgaagttggatt
taggaagctgttagatcattgagtggtgttgagagtgaagtttcactagcagggaagtttccttga
gcctaaaataaaaagaaaaaattaaaaagaatcagtttttttaattaaaaaaatagaaagctgtta
ggctcctaattcgtggggtttttttttgtaaaaacagtttagataatcctgaatgcaatcattaac
ttggttgctaattacaagaatgaaaattataatggaaaaggacaaaataatataccagctggtttg
ttattatagtccgtgtattaaaatactattgaaatacgttaaaggtaaatttttaaggtttaaaaa -continued

```
aaatttagtaacttacagggatggagaatttagatgtcagaggtggggagatttatttttataagg

taatttttatcctgataaggacttaaaaaaaagttttgcaactgaaattttaaagtaaacatgtta

agtacagttaaaaagtaagcattgtagtaaatagtggattctctggtgtgtatttttttatctcagt

gttgaaaattggaaaagaatggactgaagtctaaaaactggaataatgaaggacactaaatgcctt

tattgtagatactatgtttgtaagtctatagctaagcaacttaagccaaaaaggtctttcaactga

agctttaatcaacttattttggagatgttctcttcccttatctcatgcgtcatccctaaaataata

agatacatgggatcaaatagcccttgccttttcaacacaaatcagttggaaaattatggtttgagt

cctgttgctgccatggcttctgtttctcagaaatgagtgtgtatgaacataccaatctatgtaata

ggctaccttttttgtcttctttggaactttgtacacaaaccaagacaatatcagggtgacaggtg

aatgaacttaaattctcagtcttgtctattcaccaaaaaagtatactgcctgtttttctttaatt

attcaaggttgatgacttttaggaacatgttttatactgtatttttttaattaaagcaagtgccttg

atgtaattccatgtaaatcattgcttaaccctcttatgggatgaggatgagttattaatgtattgc

agcctactggaaaggagggggagttggttaatagcagatacttttcttctagaagcttatgtttta

tgctgtttattatgtaagatcctgtatgtgtgttgagatttagaggtttcatttgttttgtctgct

aataaattgttactctaataataaaaaaaa
```

By "SLC26A2 polypeptide" is meant a polypeptide or fragment thereof having at least about 85%, 86%, 87%, 88%, 89%, 90%, 91%, 92%, 93%, 94%, 95%, 96%, 97%, 98%, 99%, or 100% amino acid identity to NCBI Accession No. NP_000103.2 and having DNA binding activity, the polypeptide having the structure:

```
>SLC26A2_Protein
                                                  (SEQ ID NO: 2)
MSSESKEQHNVSPRDSAEGNDSYPSGIHLELQRESSTDFKQFETNDQCRP

YHRILIERQEKSDTNFKEFVIKKLQKNCQCSPAKAKNMILGFLPVLQWLP

KYDLKKNILGDVMSGLIVGILLVPQSIAYSLLAGQEPVYGLYTSFFASII

YFLLGTSRHISVGIFGVLCLMIGETVDRELQKAGYDNAHSAPSLGMVSNG

STLLNHTSDRICDKSCYAIMVGSTVTFIAGVYQVAMGFFQVGFVSVYLSD

ALLSGFVTGASFTILTSQAKYLLGLNLPRTNGVGSLITTWIHVFRNIHKT

NLCDLITSLLCLLVLLPTKELNEHFKSKLKAPIPIELVVVVAATLASHFG

KLHENYNSSIAGHIPTGFMPPKVPEWNLIPSVAVDAIAISIIGFAITVSL

SEMFAKKHGYTVKANQEMYAIGFCNIIPSFFHCFTTSAALAKTLVKESTG

CHTQLSGVVTALVLLLVLLVIAPLFYSLQKSVLGVITIVNLRGALRKFRD

LPKMWSISRMDTVIWFVTMLSSALLSTEIGLLVGVCFSIFCVILRTQKPK

SSLLGLVEESEVFESVSAYKNLQIKPGIKIFRFVAPLYYINKECFKSALY

KQTVNPILIKVAWKKAAKRKIKEKVVTLGGIQDEMSVQLSHDPLELHTIV

IDCSAIQFLDTAGIHTLKEVRRDYEAIGIQVLLAQCNPTVRDSLTNGEYC

KKEEENLLFYSVYEAMAFAEVSKNQKGVCVPNGLSLSSD
```

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methlyamine, dimethlyamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference.)

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed disclosure.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 3 shows a table listing exemplary top sensitive lines in PRISM with high expression of SLC26A2 (biomarker-positive).

FIG. 4A shows a dose curve for OVISE_OVARY. FIG. 4B shows a dose curve for A375_SKIN. FIG. 4C shows a dose curve for A673_BONE.

DETAILED DESCRIPTION OF THE DISCLOSURE

Figure 1:
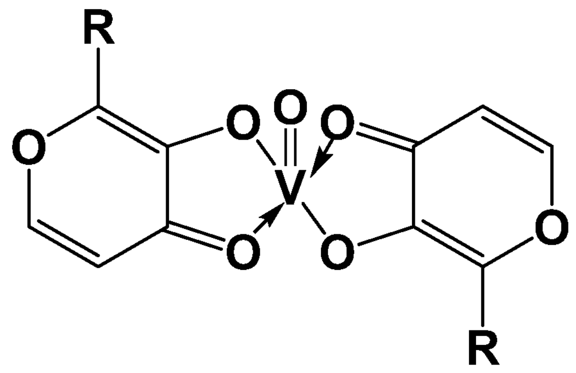
FIG. 1 shows a representative chemical structure of a vanadium containing compound with representative R substitution groups according to an exemplary embodiment of the disclosure.

The present disclosure is based, at least in part, on the discovery that certain types of cancer, particularly those characterized by high expression and/or overexpression of SLC26A2 are particularly susceptible to treatment with vanadium-containing drugs. In particular, bis(maltolato) oxovanadium(IV) (BMOV) was identified via genomic screening methods as a vanadium-containing agent among drugs present in a drug repurposing library that exhibited progressively enhanced killing of neoplasia cell lines as SLC26A2 expression levels rose across such screened neoplasia cell lines. Cancers particularly including ovarian cancer, endometrial cancer, brain cancer, bone cancer, lung cancer, and melanoma, among others, have therefore herein been identified as susceptible to treatment with vanadium-containing drugs such as, for example, BMOV, bis(ethylmaltolato)oxovanadium(IV) (BEOV), bis(isopropylmaltolato)oxovanadium(IV), (BIOV), and bis(n-butylmaltolato) oxovanadium(IV) (BnBOV) and the like. A. Such cancers particularly include ovarian cancer, bone cancer, and melanoma. The instant disclosure therefore provides compositions and methods for the diagnosis and treatment of cancer that employ vanadium-containing drugs having the general structure of Formula (I)

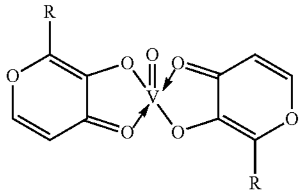

(I) (i.e., as a monotherapy, optionally in certain classes of cancer, such as SLC26A2-positive cancer) or in combination with other chemotherapeutic drugs.

The instant discovery was made using large-scale multiplex profiling of existing drugs against 578 cancer cell lines, employing a PRISM multiplexed cellular viability assay. Across more than 4,000 compounds, BMOV, BEOV, BIOV, and BnBOV were identified as agents for which high SLC26A2 transcriptional target gene expression predicted cell line sensitivity. In confirmatory studies, it was determined that SLC26A2 is both predictive and necessary for sensitivity to BMOV because CRISPR-Cas9 mediated knockout of the SLC26A2 gene rescue cells from killing by BMOV.

BMOV (and, e.g., improved and/or novel derivatives thereof) has therefore been identified as an agent for use in treating or preventing cancers that exhibit activation of and/or over-expression of SLC26A2 (particularly including ovarian cancer, endometrial cancer, brain cancer, bone cancer, lung cancer, and melanoma, notably including ovarian cancer, bone cancer, and melanoma). Expression of SLC26A2 can also be used as a predictive biomarker for such cancers and therefore a cancer's susceptibility to the agents of the instant disclosure.

BMOV is an organo-vanadium compound (OVC) that has the following structure:

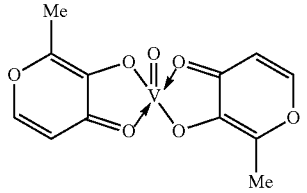

BMOV has been previously characterized as an orally available vanadium complex (OVC) that acts as an insulin mimetic. BMOV was the first OVC to be investigated for having a higher potency over inorganic vanadium salts with respect to eliciting insulin-like properties. Although the exact molecular mechanism by which BMOV elicits its insulin-mimetic effects remains unclear, several studies have shown that BMOV is a potent activator of several key components of the insulin signaling pathways, such as phosphatidyl-inositol 3-kinase (PI3-K), and its downstream effector, protein kinase B (PKB). In particular, BMOV anti-diabetic effects result from enhancement of the tyrosine-phosphorylation of insulin receptor by inhibition of the protein tyrosine phosphatase-1B (PTP-1B). In diabetic rats, BMOV has been shown to restore normoglycaemia without rising insulin levels. In this regard, BMOV is a potent phosphatase inhibitor. Exemplary dosages of BMOV include, but are not limited to, e.g., 0.01-20 mg/kg, i.v., i.p., p.o., etc.

As presented in FIG. 1, there are a number OVCs that have the general structure of Formula (I)

(I)

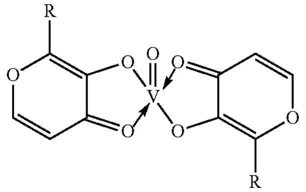

that may also be effective in treating SLC26A2-positive cancer cells.

BEOV has been previously characterized as an orally available vanadium complex that acts as an insulin mimetic. In a Phase I trial, a range of BEOV doses from 10 mg to 90 mg was given orally to non-diabetic volunteers, and resulted in no adverse effects-all biochemical parameters remained within normal limits. In the Phase IIa trial, BEOV (e.g., AKP-020) was dosed at 20 mg daily for 28 days, per os (p.o.), in seven type 2 diabetic subjects. Exemplary dosages of BEOV include, but are not limited to, e.g., 0.01-20 mg/kg, i.v., i.p., p.o., etc. BEOV has the following chemical structure:

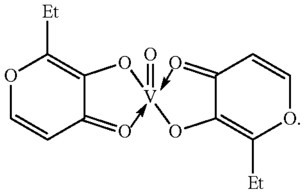

BIOV has been previously characterized as an orally available vanadium complex that acts as insulin mimetic. Exemplary dosages of BIOV include, but are not limited to, e.g., 0.01-20 mg/kg, i.v., i.p., p.o., etc. BIOV has the following chemical structure:

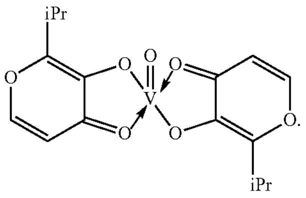

BnBOV has been previously characterized as an orally available vanadium complex that acts as insulin mimetic. Exemplary dosages of BnBOV include, but are not limited to, e.g., 0.01-20 mg/kg, i.v., i.p., p.o., etc. BnBOV has the following chemical structure:

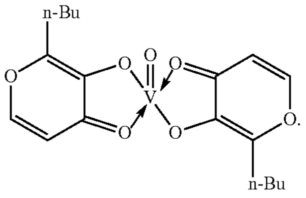

SLC26A2 was initially identified by positional cloning as the gene responsible for autosomal recessive diastrophic dysplasia (see e.g., Hastbacka J, et al. The diastrophic dysplasia gene encodes a novel sulfate transporter: positional cloning by fine-structure linkage disequilibrium mapping. Cell. 1994, 78(6):1073-1087.). The encoded protein was shown to have transport function after identifying homology with SLC26A1 and a previously identified *Neurospora* $SO_4^{2-}$ permease. A SLC26A2-based chondrodysplasia has been partially phenocopied in a Slc26a2 A386V knock-in mouse, which exhibited post-natal growth retardation, reduced mobility, and 50% mortality that was associated with skeletal abnormalities and reduced epiphyseal growth plate thickness. SLC26A2 is widely expressed in other tissues during development (Haila S. et al. SLC26A2 (diastrophic dysplasia sulfate transporter) is expressed in developing and mature cartilage but also in other tissues and cell types. J Histochem. Cytochem. 2001, 49(8):973-982.).

The SLC26A2 gene provides instructions for making a protein that transports charged molecules (ions), particularly sulfate ions, across cell membranes. This protein appears to be active in many of the body's tissues, including developing cartilage. Cartilage is a tough, flexible tissue that makes up much of the skeleton during early development. Most cartilage is later converted to bone, except for the cartilage that continues to cover and protect the ends of bones and is present in the nose and external ears.

In this regard, SLC26A2 mediates electroneutral anion exchange, accepting as substrates $SO_4^{2-}$, oxalate, $Cl^-$ (Heneghan J F et al. Regulated transport of sulfate and oxalate by SLC26A2/DTDST. Am. J. Physiol. Cell Physiol. 2010, 298(6):C1363-C1375.) and OH—, with additional capacity to transport $I^-$, $Br^-$ and $NO3^-$. The electroneural exchange mechanism accommodates $SO_4^{2-}$/oxalate exchange or divalent exchange with two monovalent anions ($SO_4^{2-}$/2Cl— or $SO_4^{2-}$/($Cl^-$+$OH^-$) (Ohana E et al. Diverse transport modes by the solute carrier 26 family of anion transporters. J. Physiol. 2009, 587(Pt 10):2179-2185.). Mutation of conserved transmembrane domain residue E417 of mouse SLC26A2 abolished transport without reducing cell surface expression. Mutation of F368 differentially altered affinities for extracellular $SO_4^{2-}$ and $Cl^-$, while leaving unchanged the SLC26A1-like positive regulation by extracellular $Cl^-$.

Cartilage cells use sulfate ions transported by the SLC26A2 protein to build molecules called proteoglycans. These molecules, which each consist of several sugars attached to a protein, help give cartilage its rubbery, gel-like structure. Because sulfate ions are required to make proteoglycans, the transport activity of the SLC26A2 protein is essential for normal cartilage formation.

It has been discovered herein that BMOV selectively kills ovarian cancer cells, bone cancer cells, and melanoma cells as well as other cancer cell types that exhibit SLC26A2 activation. BMOV shares structural similarity with other vanadium-containing compound such as, for example, BEOV, BIOV, and BnBOV. As disclosed herein, SLC26A2 expression has been identified as a predictive biomarker for drug-induced effects of the instant disclosure, and SLC26A2 was also functionally required for the observed drug responses as CRISPR-Cas9 mediated knockout of the SLC26A2 gene rescue cells from killing by BMOV.

Identification of SLC26A2 High Overexpressing Cells, Tissues and/or Cancers

Identification of a tissue, tumor and/or cancer of a subject as exhibiting elevated levels of SLC26A2 can be performed by any method available in the art. Certain methods and compositions described herein relate to identification of a cell, cell line, sample, tissue and/or subject having or at risk of developing a cancer that exhibits elevated levels of SLC26A2 at the mRNA or protein level, based upon gene-specific assessment of SLC26A2 mRNA or protein performed upon the cell, cell line, sample, tissue and/or subject having or at risk of developing a cancer that exhibits elevated levels of SLC26A2 expression. In certain embodiments, detection of elevated SLC26A2 levels can readily be performed, e.g., via assessment of mRNA expression levels (e.g., via real-time PCR or other such quantitative method). In related embodiments, assessment of SLC26A2 mRNA expression can be performed via art-recognized, oligonucleotide-mediated approaches, including, e.g., northern blotting, expression profiling using RT-PCR and/or next-generation sequencing performed upon cellular transcriptomes.

In some embodiments, detection of elevated SLC26A2 levels can readily be performed, e.g., via immunoassay for detection of SLC26A2 protein levels.

Protein levels of SLC26A2 can be quantitated in a variety of ways well known in the art, such as immunoprecipitation, Western blot analysis (immunoblotting), ELISA or fluorescence-activated cell sorting (FACS). Antibodies directed to SLC26A2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Treatable Cancers

A number of cancers have been described in the art as exhibiting elevated levels of SLC26A2. As noted herein, exemplary types of cancer that have been identified as exhibiting elevated expression of SLC26A2 include ovarian cancer, endometrial cancer, brain cancer, bone cancer, lung cancer, and melanoma. The range of cancers presently contemplated as treatable using BMOV, BEOV, BIOV, BnBOV, as described herein is not in any way limited to these aforementioned types of cancer.

As used in this context, to "treat" means to ameliorate at least one symptom of the cancer. For example, a treatment can result in a reduction in tumor size, tumor growth, cancer cell number, cancer cell growth, or metastasis or risk of metastasis.

For example, the methods can include selecting and/or administering a treatment that includes a therapeutically effective amount of BMOV, BEOV, BIOV, and/or BnBOV and/or other agents capable of selectively killing cells that exhibit high mRNA or protein expression of SLC26A2 and/or a SLC26A2 gene target. In certain embodiments, BMOV, BEOV, BIOV, and/or BnBOV and/or other agents capable of selectively killing cells that exhibit high mRNA or protein expression of SLC26A2 may be administered in combination with an additional therapeutic agent, optionally a chemotherapeutic agent including, for example, Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carfilzomib, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romidepsin, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, a salt thereof, or any combination of the foregoing.

Different chemotherapeutic agents may be preferred for use in combination with the vanadium-containing drugs described herein. For example, when used to treat ovarian cancer, the vanadium-containing drugs described herein may be combined with platinum-based drugs such as Carboplatin or Cisplatin and/or a taxane such as Paclitaxel or Docetaxel. When used to treat a lung cancer, the vanadium-containing drugs described herein may be combined with Cisplatin, Carboplatin, Docetaxel, Gemcitabine, Paclitaxel, Pemetrexed, and/or Vinorelbine. When used to treat an endometrial cancer, the vanadium-containing drugs described herein may be combined with Carboplatin, Cisplatin, Doxorubicin or liposomal Doxorubicin, and/or Paclitaxel. When used to treat brain cancer, the vanadium-containing drugs described herein may be combined with Carmustine, Lomustine, Procarbazine, Temozolomide, and/or Vincristine. When used to treat a bone cancer, the vanadium-containing drugs described herein may be combined with Cisplatin, Cyclophosphamide, Doxorubicin, Etoposide, Ifosfamide, Methotrexate, and/or Vincristine. When used to treat a melanoma, the vanadium-containing drugs described herein may be combined with Carboplatin, Cisplatin, Dacarbazine, Nab-paclitaxel, Paclitaxel, Temozolomide, and/or Vinblastine.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the IC50 (i.e., the concentration of BMOV, BEOV, BIOV, and/or BnBOV, which achieves a half-maximal inhibition of symptoms and/or a half-maximal extent of killing of targeted cancer cells) as determined in cell culture. Such information can be used to more accurately determine useful doses in humans. Levels in plasma may be measured, for example, by high performance liquid chromatography.

Combination Treatments

The compositions and methods of the present disclosure may be used in the context of a number of therapeutic or prophylactic applications. In order to increase the effectiveness of a treatment with the compositions of the present disclosure, e.g., BMOV, BEOV, BIOV, and/or BnBOV can be selected and/or administered as a single agent, or to augment the efficacy of another therapy (second therapy), it may be desirable to combine these compositions and methods with one another, or with other agents and methods effective in the treatment, amelioration, or prevention of diseases and pathologic conditions, for example, cancers characterized by high SLC26A2 expression levels (e.g., an ovarian cancer, an endometrial cancer, a brain cancer, a bone cancer, a lung cancer, and a melanoma).

In certain embodiments of the instant disclosure, one or more chemotherapeutic drugs that are unrelated to BMOV, BEOV, BIOV, and/or BnBOV can be co-administered with BMOV, BEOV, BIOV, and/or BnBOV or related compound, or can be administered in advance of BMOV, BEOV, BIOV, and/or BnBOV or related compound administration.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing cancer, e.g., a cancer that exhibits high SLC26A2 or high SLC26A2 gene target expression and/or is a luminal or ER-positive form of breast cancer) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as BMOV, BEOV, BIOV, and/or BnBOV, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with BMOV, BEOV, BIOV, and/or BnBOV) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 μg/kg, followed by a weekly maintenance dose of about 100 μg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 μg/kg to about 2 mg/kg (such as about 3 μg/kg, about 10 μg/kg, about 30 μg/kg, about 100 μg/kg, about 300 μg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., BMOV, BEOV, BIOV, and/or BnBOV) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Drugs provided herein can be formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for oral delivery or intravenous injection to a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., BMOV, BEOV, BIOV, and/or BnBOV) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

A drug or other therapy of the instant disclosure is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 μg/kg/day, at least 100 μg/kg/day, at least 250 μg/kg/day, at least 500 μg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 μg/kg/day, and less than 500 μg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., BMOV, BEOV, BIOV, and/or BnBOV) described herein. In certain embodiments, a dose described herein includes independently between 1 mg and 3 mg, inclusive, of an agent (e.g., BMOV, BEOV, BIOV, and/or BnBOV) described herein. In certain embodiments, a dose described herein includes independently between 3 mg and 10 mg, inclusive, of an agent (e.g., BMOV, BEOV, BIOV, and/or BnBOV) described herein. In certain embodiments, a dose described herein includes independently between 10 mg and 30 mg, inclusive, of an agent (e.g., BMOV, BEOV, BIOV, and/or BnBOV) described herein. In certain embodiments, a dose described herein includes independently between 30 mg and 100 mg, inclusive, of an agent (e.g., BMOV, BEOV, BIOV, and/or BnBOV) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., BMOV, BEOV, BIOV, and/or BnBOV) or composition, as described herein, can be administered in combination with one or more additional pharmaceutical agents (e.g., therapeutically and/or prophylactically active agents), which are different from the agent or composition and may be useful as, e.g., combination therapies.

The agents or compositions can be administered in combination with additional pharmaceutical agents that improve their activity (e.g., activity (e.g., potency and/or efficacy) in treating a disease (e.g., cancer) in a subject in need thereof, in preventing a disease in a subject in need thereof, in reducing the risk of developing a disease in a subject in need thereof, etc. in a subject or cell. In certain embodiments, a pharmaceutical composition described herein including an agent (e.g., BMOV, BEOV, BIOV, and/or BnBOV) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an immunotherapy, an antioxidant, an anti-inflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, additional BMOV derivatives, BEOV derivatives, BIOV derivatives, BnBOV derivatives, other anti-cancer agents, immunotherapy and/or immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure Kits of the instant disclosure may include one or more containers comprising an agent (e.g., BMOV, BEOV, BIOV, and/or BnBOV) of this disclosure and/or may contain agents (e.g., oligonucleotide primers, probes, etc.) for identifying a cancer or subject as having a cancer and/or as exhibiting elevated SLC26A2 levels. In some embodiments, the kits further include instructions for use in accordance with the methods of this disclosure. In some embodiments, these instructions comprise a description of administration of the agent to treat or diagnose, e.g., a cancer that exhibits elevated expression of SLC26A2 s, according to any of the methods of this disclosure in some embodiments, the instructions comprise a description of how to detect a cancer or subject as exhibiting elevated SLC26A2 levels, for example in an individual, in a tissue sample, or in a cell. The kit may further comprise a description of selecting an individual suitable for treatment based on identifying whether that subject has a cancer that exhibits elevated SLC26A2 levels.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a cancer or subject having a cancer exhibiting elevated SLC26A2 levels, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like.

Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is BMOV, BEOV, BIOV, and/or BnBOV. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

PRISM Screening

Parental cell lines were obtained from the Cancer Cell Line Encyclopedia (CCLE) project (1). PRISM cell line barcoding, pooling, and screening was performed as previously described with several improvements to the original method (2). First, the lentiviral vector was modified to encode the unique barcode identifier at the end of the puromycin resistance gene. This enables barcodes to be detected using a variant of the mRNA capture and Luminex detection method developed for the L1000 gene expression assay (3). Second, a set of ten inert barcodes were spiked-in to each well of each plate after cell lysis to control for variation in PCR amplification as detailed below.

Data Processing

Luminex technology produced .Ixb files containing data for each Luminex bead observed during detection. These .Ixb files were processed to compute Median Fluorescence Intensity (MFI) values, calculated as the median of the values obtained for all beads corresponding to a single PRISM barcode.

MFI values were log-transformed (logMFI) and used to perform basic quality control. To detect probable screening artifacts, logMFI values were centered to the median logMFI for each cell line on each plate in order to put the measurements from each cell line on the same scale. For each well on each plate, the median of these centered values was then standardized according to the global median and global MAD across all plate wells in the same position. Data from wells with a standardized score of greater than 5 or less than −5 were excluded from all further processing steps.

For each cell line on each plate, the distribution of MFI values observed for the DMSO-treated negative controls was compared to that of the positive controls using a robust form of the Strictly Standardized Mean Difference (SSMD*)'. Specifically, SSMD* was calculated as:

$$\frac{(\mu_- - \mu_+)}{\sqrt{\sigma_-^2 + \sigma_+^2}}$$

Data corresponding to SSMD values less than 2 were removed before calculating cell viability.

The data in the instant disclosure were produced according to two different screening protocols. In the PR500 protocol, ten inert barcodes were spiked-in to each well of each plate after cell lysis. For data produced using the PR500 protocol, normalized MFI (nMFI) values were computed by taking the ratio of each MFI value against the median of the inert barcodes within each well. For data produced before the PR500 protocol was introduced, nMFI values were set equal to MFI values.

Cell viability was calculated as the ratio of nMFI to the median of the nMFI from the DMSO-treated negative controls for each cell line on each plate. Batch effects produced from variable detection and assay conditions were then removed using ComBat (4). The final viability values were calculated as the median of the batch-corrected cell viabilities from biological replicates for each cell line, compound and dose.

Dose Response

Measures of dose response were obtained by fitting 3-parameter logistic curves to viability values for each compound and cell line using the R package 'drc'. Following the practice of Smirnov and Safikhani (5), viability was truncated at 1.0 and fit as a function of drug concentration according to:

$$V(c) = E_\infty + \frac{1 - E_\infty}{1 + e^{HS(c - EC50)}}$$

where all concentrations are in the natural logarithm scale. IC50 values were defined as the concentration c at which V(c)=0.5, given by the formula:

$$IC50 = -\frac{\log(1 - 2E_\infty)}{HS} + EC50$$

The Area Under the dose response Curve (AUC) was calculated using the normalized integral:

$$\frac{\int_{c_{min}}^{c_{max}} V(c)dc}{c_{max} - c_{min}}$$

where $$\int V(c)dc = \frac{(E_\infty - 1)\log(1 + e^{-HS(c-EC50)})}{HS} + E_\infty c + const$$

The formulation above puts AUC values on a scale between 0 and 1, where lower AUC values indicate increased sensitivity to the treatment.

Nomination for Secondary Screen

Compounds from the primary screen were labeled as candidates for secondary screening using a combination of cell killing metrics and goodness-of-fit measures obtained from the ATLANTIS method (6). Metrics considered were profile mean, variance, skewness, number of sensitive cell lines as well as the 75th, 25th, 10th and 5th quantiles of each profile's distribution. Cell lines were defined as sensitive to a compound if their median log fold change after batch correction was below 2 standard deviations of the distribution of DMSO controls. ATLANTIS model R2 values of above 0.1 were considered strong models. Subject to compound availability and manual curation, candidates were progressed to secondary profiling at 8 point dose.

Antibodies and Reagents

SLC26A2 antibody was obtained from Bethyl Laboratories, Inc. (A304-466A.

Cell Lines

Cell lines were obtained from the Cancer Cell Line Encyclopedia (CCLE) project at the Broad Institute.

Cloning

XP003, XP023, psPAX, and pMD2.G vectors were acquired from the Broad Genetic Perturbation Platform (GPP). Oligos for sgRNAs designs were generated using Broad GPP sgRNA guide generator resource (on the World Wide Web at (www)broad institute.org/gpp/db/analvsis-tools/sgrna-design) and the respective oligos were synthesized by Integrated DNA Technologies. In order to clone the sgRNAs into either the XPR003 guide only or XPRO23 all-in-one crispr lentiviral expression systems the protocol available on the Broad GPP website (www.broadinstitute.org/gpp/db/resources/protocols) was followed.

Viral Vector Generation

In order to generate viral vectors, HEK293T cells were seeded in 6 well plates at a density of 1.5E6 cells per well. Cells were then transfected with a mixture of TranslT@-LT1 Transfection Reagent (MirusBio #M1R2304), psPAX2, pMD2.G, lentiviral plasmid diluted in Opti-MEM™ (Thermo #31985062). The following day media was changed DMEM (Thermo #10566016) with 30% FBS (Sigma 18A079). 72 hrs after transfection, virus containing media was collected and run through a 0.2 uM filter to remove cellular debris. Virus was aliquoted and stored short term at −20 C until infection day.

Lentiviral Infection

A mixture of 3E6 cells, virus, and media with 4 μg/mL polybrene (Millipore) at a total volume of 2 mL was plated per well of a 12 well plate. Cells were centrifuged at 2000 RPM for 2 hours at 30° C. After removal from incubator, 2 mL of fresh media was added to each well and cells were allowed to incubate at 37° C. overnight. The following day cells were selected for with puromycin for 3-10 days, or until the non-infected control cell were completely non-viable.

CellTiter-Glo® Cellular Viability Assay

Cell viability was assayed using a modified manufacturer's protocol for CellTiter-Glo® (Promega #G7573). Cells were seeded at a density of 2000 cells per well in a 96 well black, clear bottom plate (Corning #89091-012) in 100 uL total media per well. The following day different concentrations of compounds at various doses were printed in triplicate in a random well format using the Tecan D300e Digital Dispenser. After 120H, 60 μL of a 1:3 solution of CellTiterGlo reagent in 1×PBS (Corning #01018002) was added per well and allowed to incubate at RT for 10 mins. Luminescence was measured with an integration time of 0.1 s using Envision Microplates Reader (PERKIN ELMER #2105-0010). Biological replicates were averaged and normalized to vehicle control. Dose curves were generated using Graphpad Prism.

Western Immunoblotting

Adherent cells were washed once with cold 1×PBS (Corning #01018002) and lysed with RIPA buffer (Sigma #R0278) supplemented by protease and phosphatase inhibitors (Sigma). Protein content was quantified using the DC Protein Assay (BioRad #5000111). Samples were reduced with (loading buffer) and boiled at 95° C. before being resolved by SDS gel electrophoresis on 4-20% Tris/glycine gels (Invitrogen). Proteins were transferred using the IBlot2 (Thermo #IB21001) onto the iBlot™2 nitrocellulose Transfer Stacks (Thermo #IB23001). The membranes were then blocked in Odyssey Blocking Buffer (Li-COR #927-40000) for one hour, and then probed overnight with primary antibodies diluted in blocking buffer. The following day, membranes were washed 3×5 mins with 1×TBST and then probed with LiCOR Infrared secondary antibodies for 1 hour at room temperature. Membranes were washed an additional 3×5 mins in 1×TBST and then imaged using the LiCOR Imager.

Figure 2:
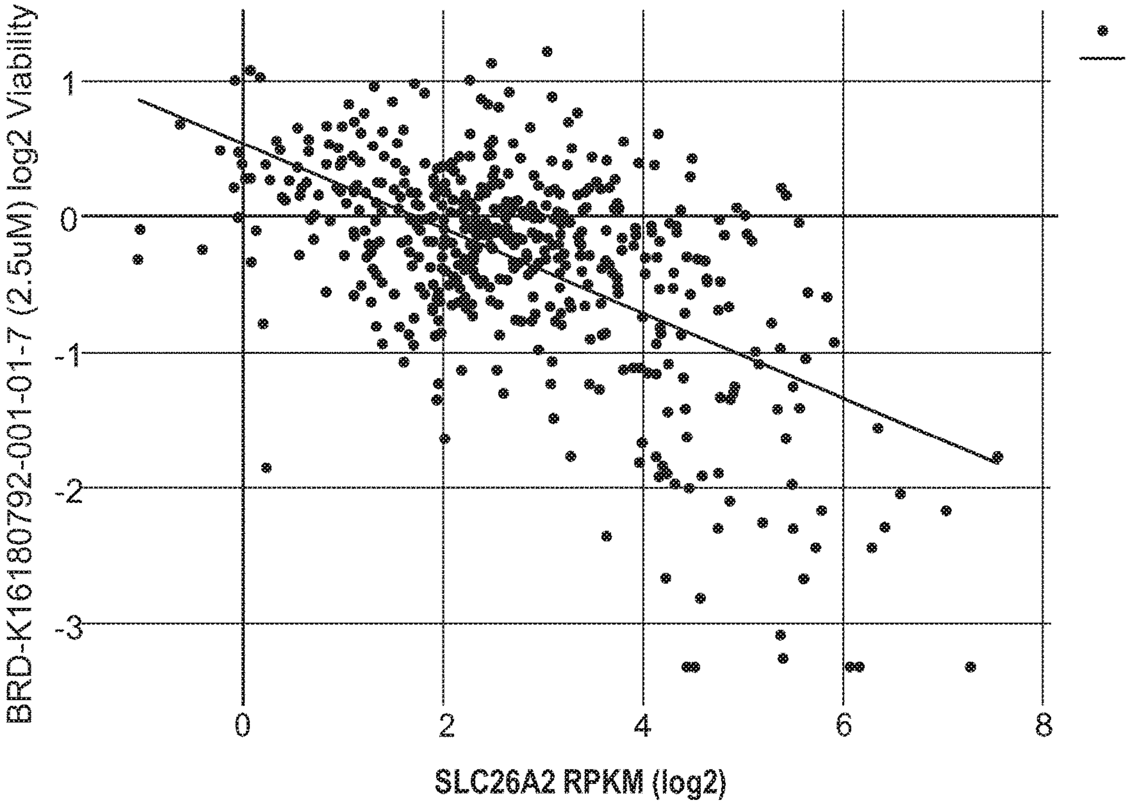
FIG. 2 shows a dot plot of killing by a vanadium-containing drug, bis(maltolato)oxovanadium(IV) (BMOV), predicted by high SLC26A2 expression.

Example 2: PRISM Screening Identified Known Insulin Mimetics as Cytotoxic to SLC26A2-Dependent Cancer Cell Lines PRISM screening was applied to a drug repurposing library (described in Corsello et al. *Nat. Medicine* 23: 405-408), to identify compounds that were selectively capable of killing cancer cell lines characterized by elevation of SLC26A2 and/or SLC26A2 target mRNA and/or protein expression levels. BMOV was observed to exhibit a shared cell killing profile specific for such SLC26A2-dependent cancer cell lines (see e.g., FIG. 3), a profile distinct from those observed for other compounds of the input cell repurposing library. The top expression features identified for cytotoxicity effects observed for BMOV, which validated the SLC26A2-dependency of such compound-mediated cytotoxic effects (FIGS. 2-3).

SLC26A2 has been previously characterized as a transporter. It has been identified as highly expressed in ovarian cancer, endometrial cancer, brain cancer, bone cancer, lung cancer, and melanoma. The instant studies demonstrated SLC26A2 to be a lineage-specific cancer dependency for luminal breast cancer, via CRISPR-Cas9 knockout of SLC26A2 in various cell lines possessing highly varying native levels of SLC26A2 expression (FIG. 3). In particular, BMOV exhibited a selective killing pattern across tested cell lines, with enrichment for luminal breast cancer cell lines (FIG. 4). Furthermore, BMOV showed selective killing of SLC26A2-high cancer cell lines, as compared to assayed cancer cell lines that possessed lower SLC26A2 expression levels (FIG. 5).

Example 3: BMOV Cancer Cell Killing Requires SLC26A2 Protein Expression

It was then examined whether knockout of SLC26A2 in BMOV-sensitive cancer cells could rescue such knockout breast cancer cells from SLC26A2 cytotoxicity. Initially, CRISPR-Cas9-mediated knockout of the SLC26A2 gene was performed in SLC26A2-susceptible cancer cell lines OVISE_OVARY (FIG. 3). These results indicated that while SLC26A2 expression might serve as a predictive biomarker for certain breast cancers, the presence of SLC26A2 was functionally required for the BMOV cytotoxic drug response observed.

Example 4: Therapeutic Testing of SLC26A2

The cytotoxic activity of BMOV, and or derivatives of any of the aforementioned compounds is tested in in vivo xenograft models (optionally mouse xenograft models), with the downstream mechanism for SLC26A2 (or other agent and/or derivative)-induced cell death thereby further investigated. Additional derivatives of BMOV, (e.g., BEOV, BIOV, BnBOV, are also synthesized and tested for cell killing activity.

Figure 4A:
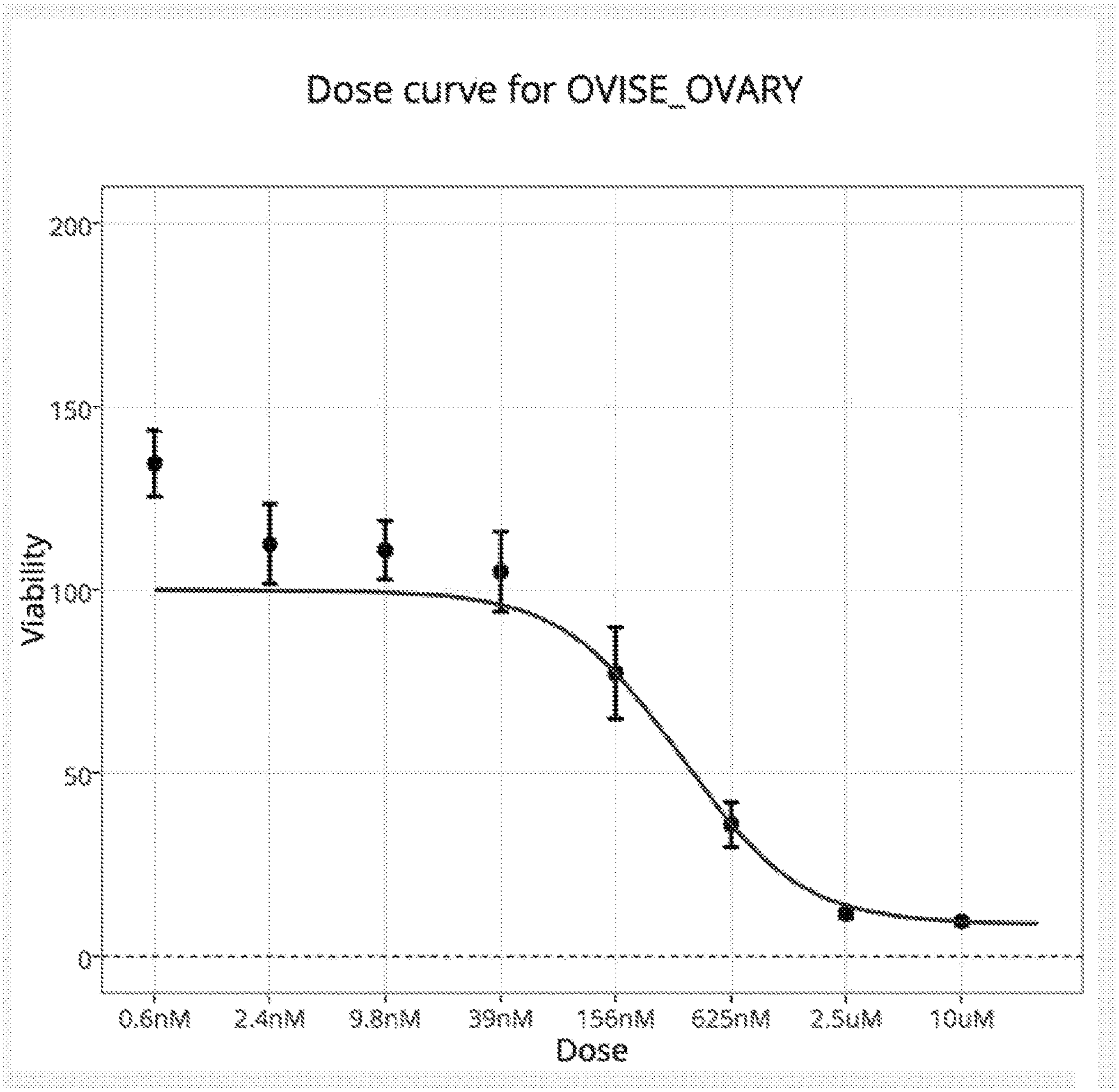
FIGS. 4A-4C shows three exemplary dose curves for BMOV the sensitive lines in PRISM.
Figure 4B:
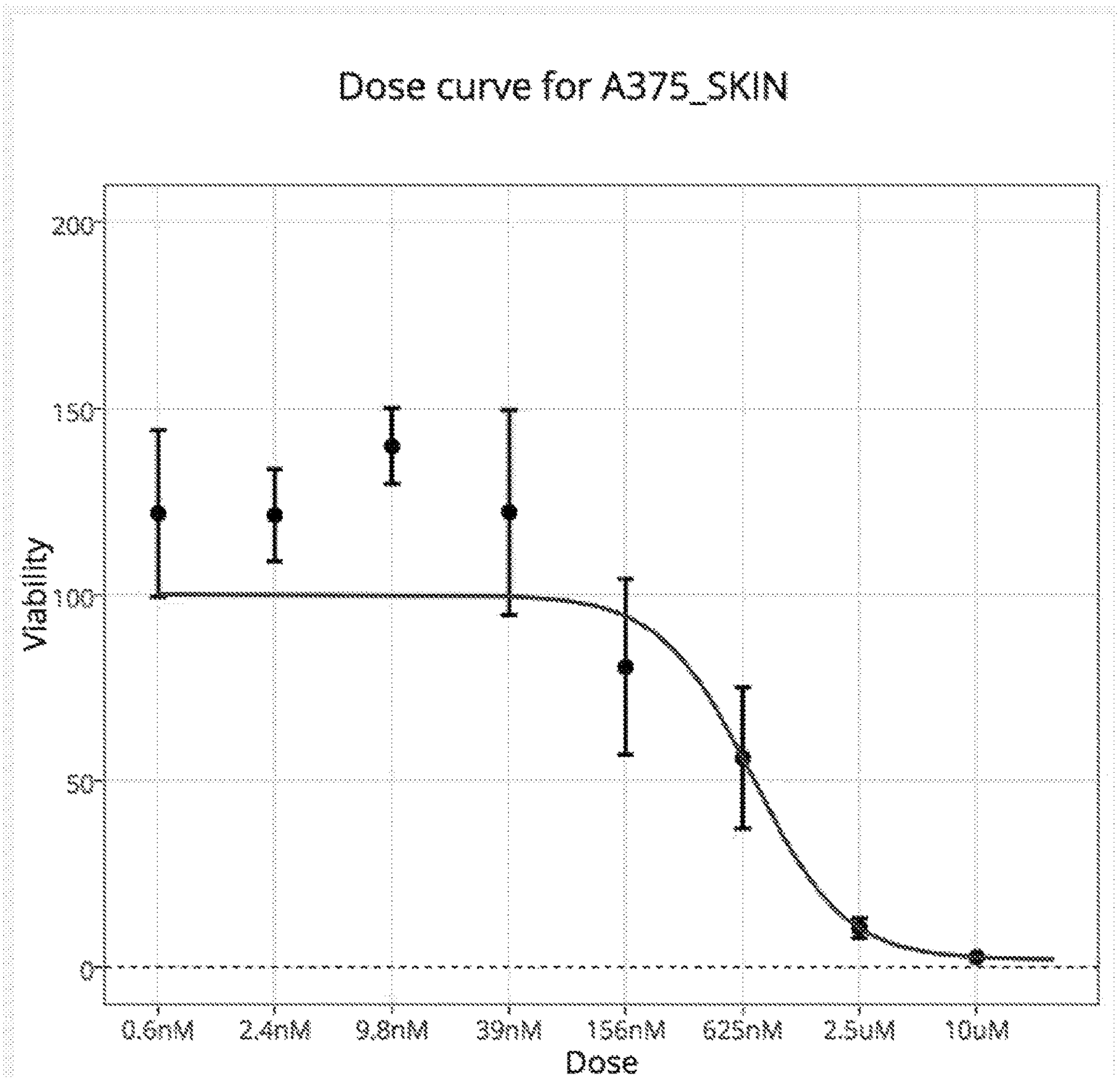
Figure 4C:
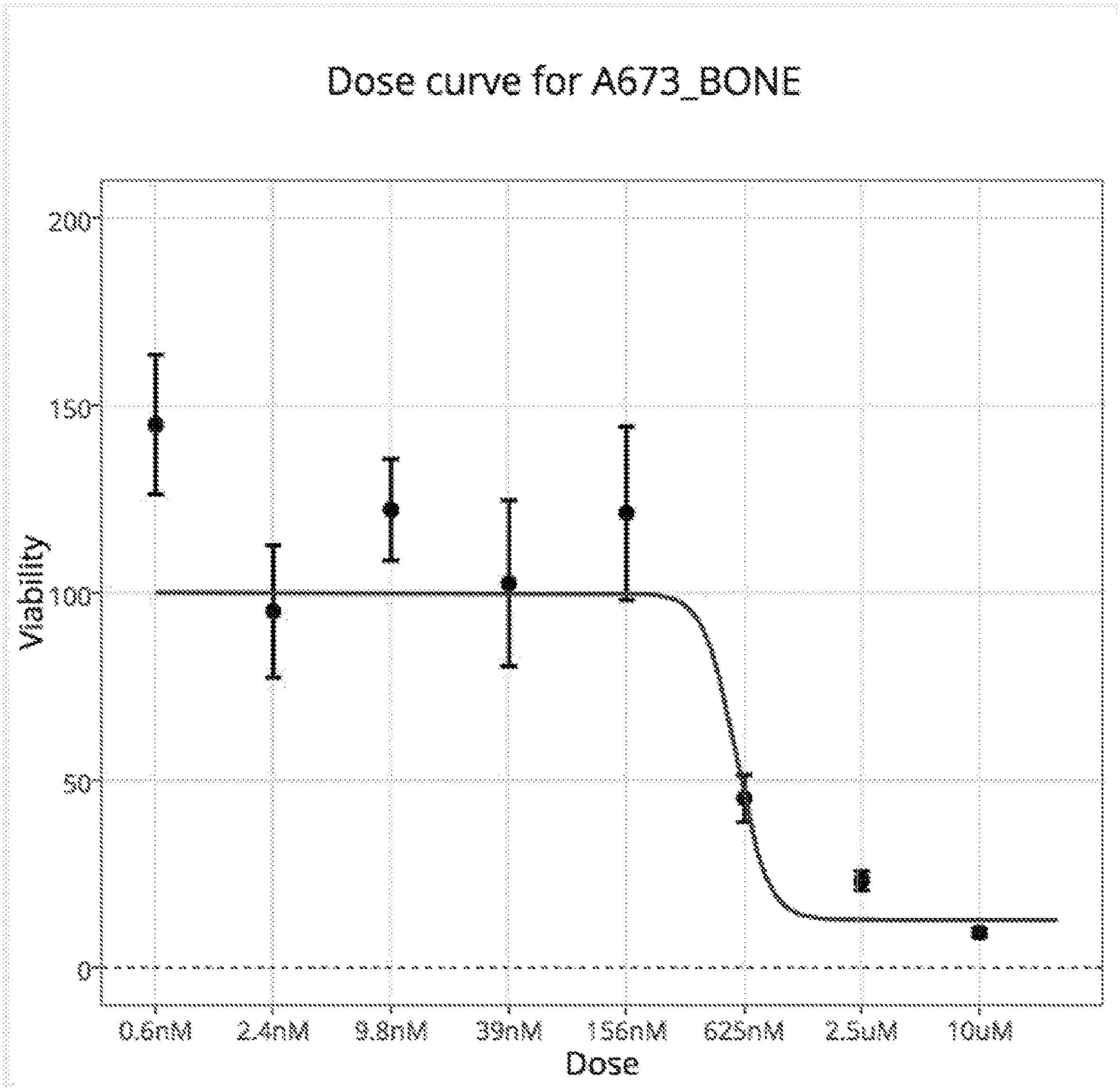
Figure 5:
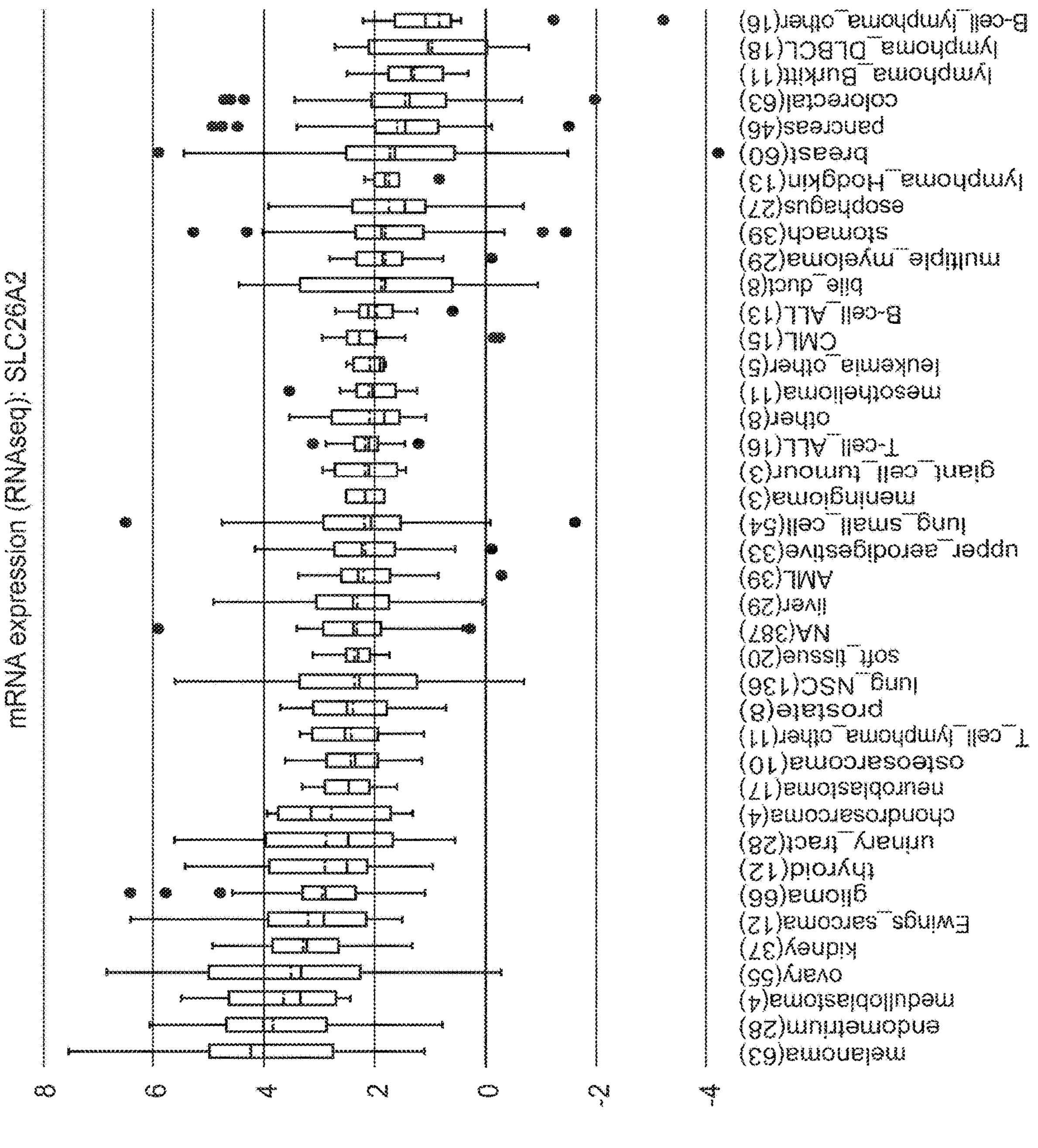
FIG. 5 shows a box plot of SLC26A2 mRNA expression data from the Cancer Cell Line Encyclopedia (CCLE) data set.

As shown in FIGS. 4A-4C, the techniques herein provide the ability for BMOV, along with related derivative compounds, the sensitive lines in PRISM. FIG. 4A shows a dose curve for OVISE_OVARY. FIG. 4B shows a dose curve for A375_SKIN. FIG. 4C shows a dose curve for A673_BONE.

Figure 6:
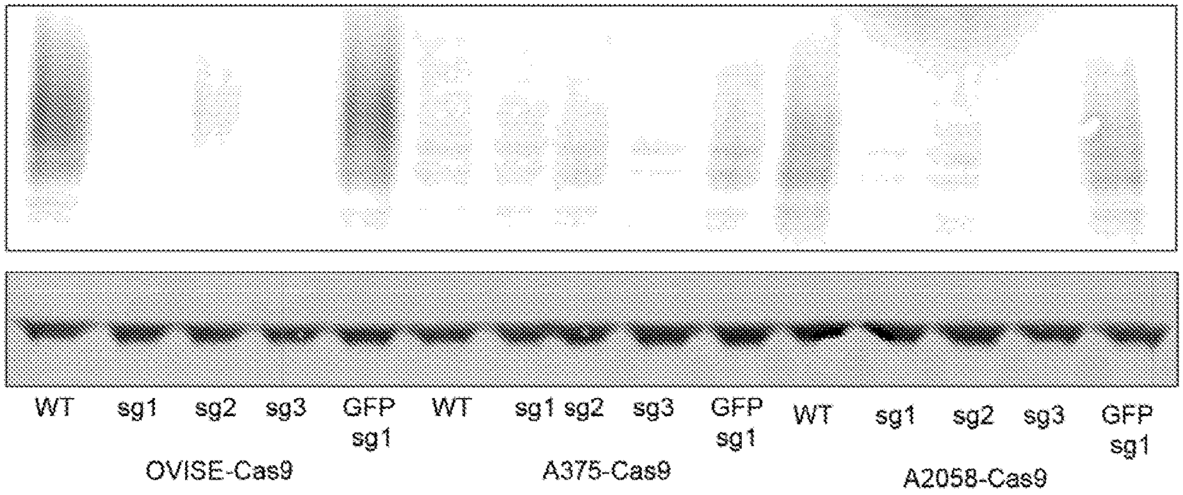
FIG. 6 shows a Western Blot displaying SLC26A2 protein expression levels in CRISPR knockouts in OVISE, A375, and A2058 cell lines (WT=wildtype, sg=single guide RNA, and GFP=green fluorescent protein).

FIG. 6 shows a Western Blot displaying SLC26A2 protein expression levels in CRISPR knockouts in OVISE, A375, and A2058 cell lines (WT=wildtype, sg=single guide RNA, and GFP=green fluorescent protein).

Figure 7A:
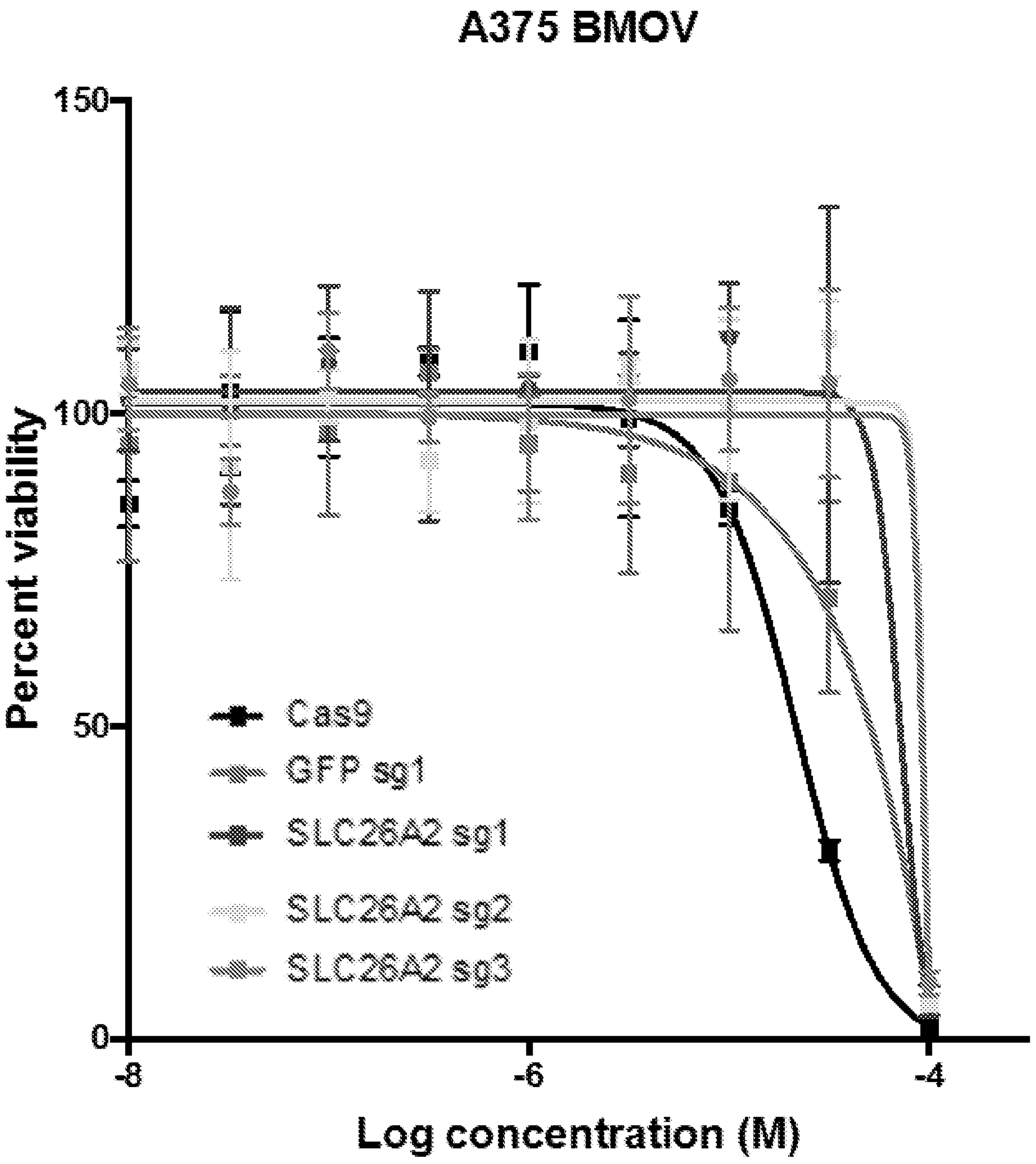
FIGS. 7A-7C are viability curves showing that SLC26A2 knockouts rescue BMOV sensitivity. Percent viability vs. log concentration (M) BMOV graphs for SLC26A2 knockouts in A375, OVISE, and A2058 cell lines are shown in FIG. 7A, FIG. 7B, and FIG. 7C, respectively.
Figure 7B:
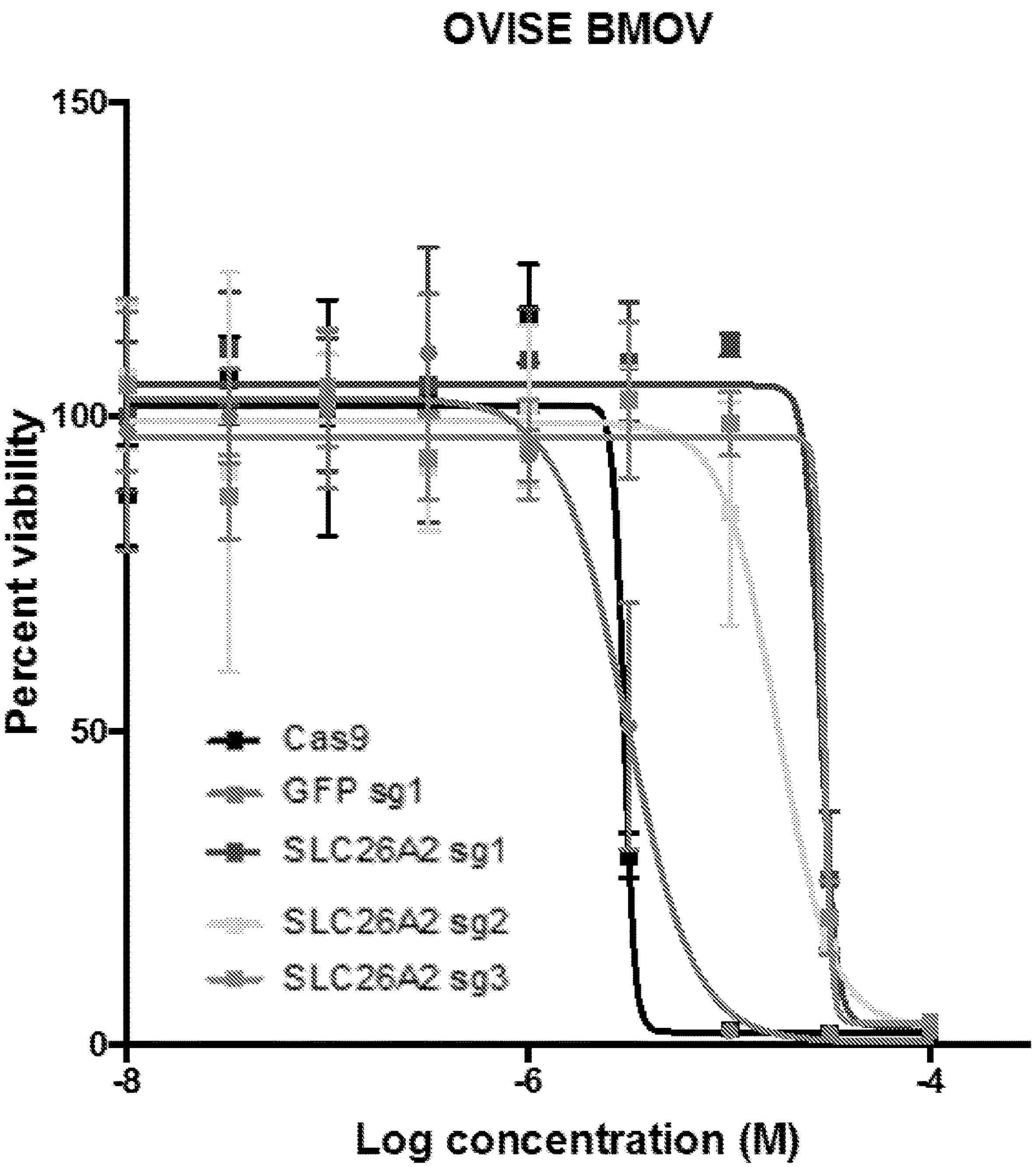
Figure 7C:
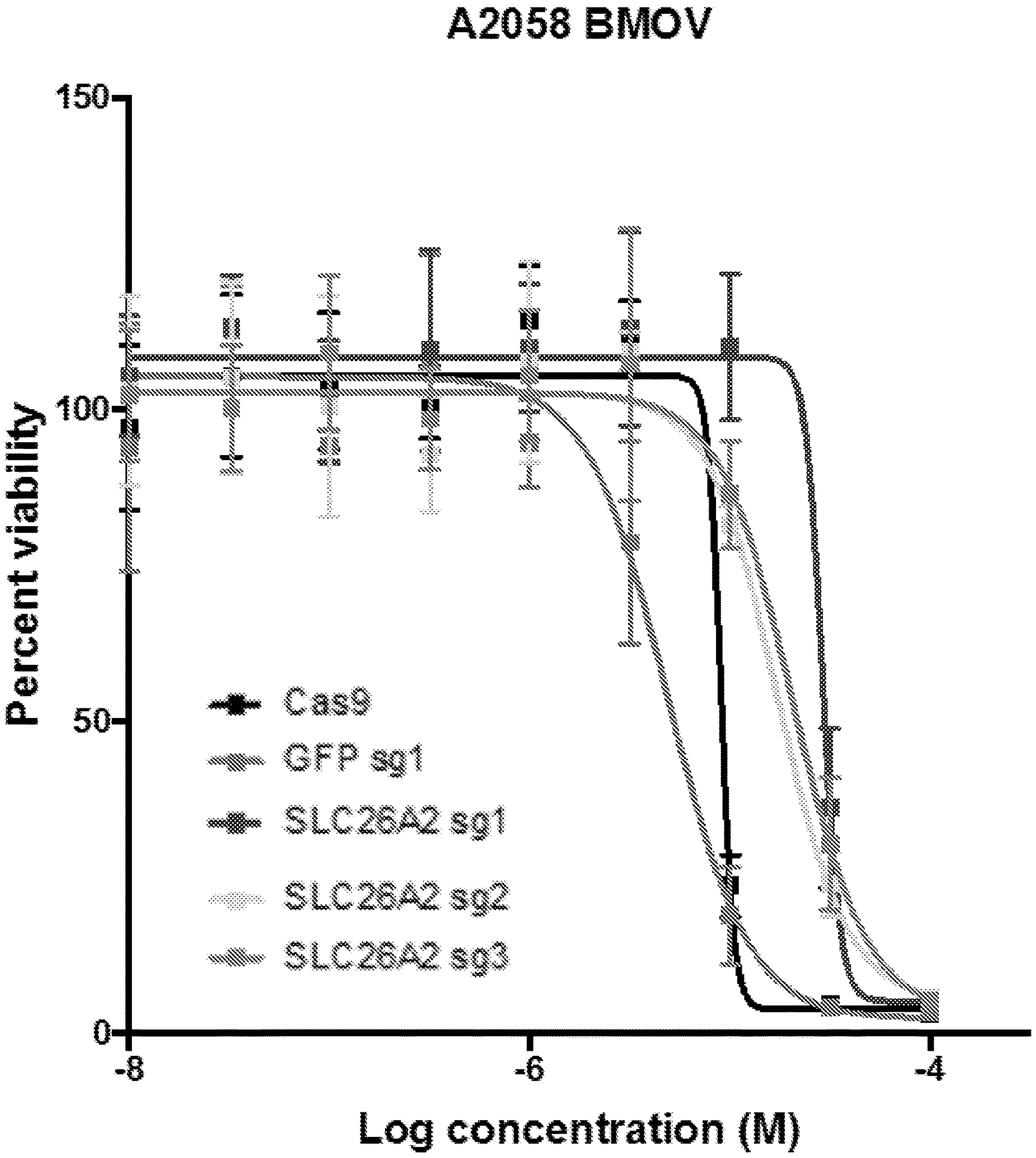

FIGS. 7A-7C present viability curves showing that SLC26A2 knockouts rescue BMOV sensitivity. Percent viability vs. log concentration (M) BMOV graphs for SLC26A2 knockouts in A375, OVISE, and A2058 cell lines are shown in FIG. 7A, FIG. 7B, and FIG. 7C, respectively.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms “a” and “an” and “the” and similar referents in the context of describing the disclosure (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosure. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the disclosure disclosed herein without departing from the scope and spirit of the disclosure. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

What is claimed is:

1. A method for selecting a treatment for a subject having a Solute Carrier Family 26 Member 2 (SLC26A2) positive cancer, the method comprising:

(a) identifying a sample of the subject to possess elevated SLC26A2 mRNA expression levels, as compared to an appropriate control, thereby identifying the subject as having the SLC26A2 positive cancer; and (b) selecting a compound of Formula (I)

(I)

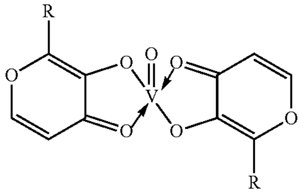

as the treatment for the subject identified as having the SLC26A2 positive cancer.

2. The method of claim 1, wherein R is selected from the group consisting of $CH_3$, $C_2H_5$, i-$C_3H_7$, and n-$C_4H_9$.

3. The method of claim 1, wherein the cancer is selected from the group consisting of an ovarian cancer, an endometrial cancer, a brain cancer, a bone cancer, a lung cancer, and a melanoma.

4. The method of claim 1, wherein

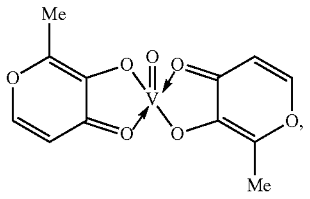

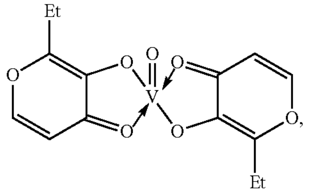

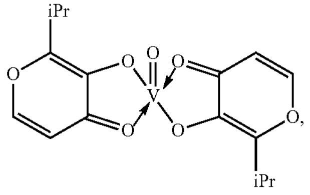

or

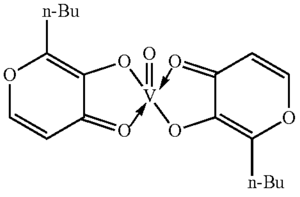

is selected as a treatment for the subject.

5. The method of claim 1, further comprising: (c) administering the selected compound of Formula (I)

(I)

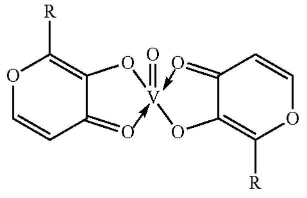

to the subject.

6. The method of claim 5, wherein the compound of formula (I) is

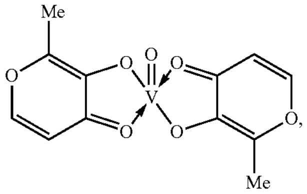

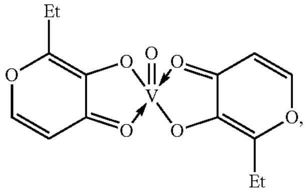

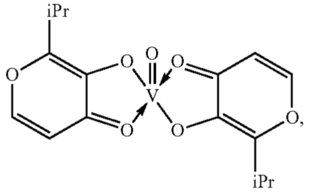

or

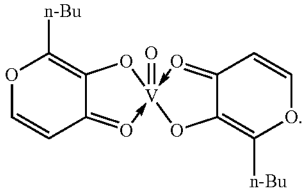

7. The method of claim 5, wherein the compound of formula (I) is

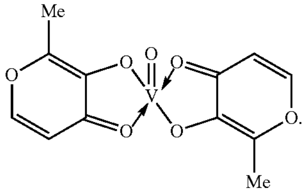

8. The method of claim 1, wherein the subject is human.

9. The method of claim 5, wherein the compound of Formula (I) is administered in combination with an additional therapeutic agent.

10. The method of claim 9, wherein the additional therapeutic agent is Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carfilzomib, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romidepsin, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, a salt thereof, or any combination of the foregoing.

11. The method of claim 5, wherein the cancer is ovarian cancer and wherein the compound of Formula (I) is administered in combination with a platinum-based drug, Carboplatin, Cisplatin, a taxane, Paclitaxel, or Docetaxel.

12. The method of claim 5, wherein the cancer is lung cancer and wherein the compound of Formula (I) is administered in combination with Cisplatin, Carboplatin, Docetaxel, Gemcitabine, Paclitaxel, Pemetrexed, or Vinorelbine.

13. The method of claim 5, wherein the cancer is endometrial cancer and wherein the compound of Formula (I) is administered in combination with Carboplatin, Cisplatin, Doxorubicin or liposomal Doxorubicin, or Paclitaxel.

14. The method of claim 5, wherein the cancer is brain cancer and wherein the compound of Formula (I) is administered in combination with Carmustine, Lomustine, Procarbazine, Temozolomide, or Vincristine.

15. The method of claim 5, wherein the cancer is bone cancer and wherein the compound of Formula (I) is administered in combination with Cisplatin, Cyclophosphamide, Doxorubicin, Etoposide, Ifosfamide, Methotrexate, or Vincristine.

16. The method of claim 5, wherein the cancer is melanoma and wherein the compound of Formula (I) is administered in combination with Carboplatin, Cisplatin, Dacarbazine, Nab-paclitaxel, Paclitaxel, Temozolomide, or Vinblastine.

17. A method for selecting a treatment for a subject having a Solute Carrier Family 26 Member 2 (SLC26A2) positive cancer, the method comprising:

(a) identifying a sample of the subject to possess elevated SLC26A2 mRNA expression levels, as compared to an appropriate control, thereby identifying the subject as having the SLC26A2 positive cancer; and (b) selecting a compound of Formula (I)

(I)

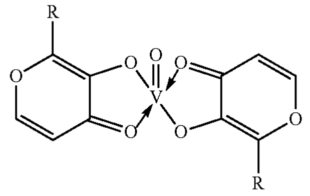

as the treatment for the subject identified as having SLC26A2 positive cancer, wherein R is selected from the group consisting of $CH_3$, $C_2H_5$, i-$C_3H_7$, and n-$C_4H_9$.

18. A method for selecting a treatment for a subject having a Solute Carrier Family 26 Member 2 (SLC26A2) positive cancer, the method comprising:

(a) identifying a sample of the subject to possess elevated SLC26A2 mRNA expression levels, as compared to an appropriate control, thereby identifying the subject as having SLC26A2 positive cancer;

(b) selecting a compound of Formula (I)

(I)

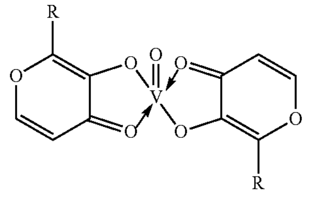

as the treatment for the subject identified as having SLC26A2 positive cancer, wherein R is selected from the group consisting of $CH_3$, $C_2H_5$, i-$C_3H_7$, and n-$C_4H_9$; and (c) administering the selected compound of Formula (I) to the subject.

* * * * *